(12) United States Patent
Amir et al.

(10) Patent No.: US 12,233,176 B2
(45) Date of Patent: Feb. 25, 2025

(54) DISINFECTION DEVICE

(71) Applicants: Naor Amir, Plantation, FL (US); Shawn Darrell Chriswell, Longmont, CO (US); Hanna Robla, Miami, FL (US); Altrese Hawkins, Pembroke Pines, FL (US); Sandi Glauser, Parkland, FL (US)

(72) Inventors: Naor Amir, Plantation, FL (US); Shawn Darrell Chriswell, Longmont, CO (US); Hanna Robla, Miami, FL (US); Altrese Hawkins, Pembroke Pines, FL (US); Sandi Glauser, Parkland, FL (US)

(73) Assignee: Naor Amir, Plantation, FL (US)

( * ) Notice: Subject to any disclaimer, the term of this patent is extended or adjusted under 35 U.S.C. 154(b) by 376 days.

(21) Appl. No.: 17/684,456

(22) Filed: Mar. 2, 2022

(65) Prior Publication Data
US 2023/0277700 A1  Sep. 7, 2023

(51) Int. Cl.
*A61L 2/10* (2006.01)
*A61L 2/24* (2006.01)

(52) U.S. Cl.
CPC ............ *A61L 2/10* (2013.01); *A61L 2/24* (2013.01); *A61L 2202/11* (2013.01); *A61L 2202/122* (2013.01); *A61L 2202/14* (2013.01); *A61L 2202/16* (2013.01); *A61L 2202/26* (2013.01)

(58) Field of Classification Search
CPC .. A61L 2/10; A61L 2202/122; A61L 2202/16; A61L 9/20; A61L 2/24; A62B 18/02; A62B 25/00; A45C 2011/007; A45C 11/00; A41D 13/11
See application file for complete search history.

(56) References Cited

U.S. PATENT DOCUMENTS

2022/0008583 A1* 1/2022 Garcia .................. A23B 7/015

OTHER PUBLICATIONS

CN_212756483_U (Year: 2021).*
CN_213284604_U (Year: 2021).*
KR_20210111088_A (Year: 2021).*
KR_20210112973_A (Year: 2021).*

* cited by examiner

*Primary Examiner* — Michael J Logie

(57) ABSTRACT

The present invention is directed to a portable, rechargeable, sanitation device that easily disinfects masks, as well as other items, by inactivating viruses and bacteria present on the mask's surface via exposure to UVC light. This sterilization device is composed of a mechanical case to storing the mask, a novel fastening device to ensure mask is properly secured in place for maximum sanitation effect, an optical component consisting of multiple UVC LEDs, a rechargeable power source, and a visual display that indicates the sanitation and lighting status of the device. This device will encourage adoption of reusable masks as opposed to one-time use, reducing costs of purchasing multiple masks as well environmental impact produced by single use waste. The device will ensure an easy solution for proper and frequent sanitation of face masks, meeting current CDC guidelines. Kits comprising the device and one or more attachment or mounting apparatus are also provided herein.

8 Claims, 19 Drawing Sheets

DISINFECTION DEVICE

CROSS REFERENCES TO RELATED APPLICATIONS

The present application claims the benefit and priority of U.S. provisional application No. 63/160,567, filed Mar. 12, 2021.

FIELD OF INVENTION

The present invention relates generally to a portable, rechargeable, sanitation device that easily disinfects masks by inactivating viruses and bacteria present on the face mask's surface via exposure to UVC light.

BACKGROUND

Large proportions of the public have recently adopted the use of reusable face masks due to the 2020 SARS-CoV-2, also known as Covid-19, pandemic. Continued use of these face masks has been encouraged by State, County, and Federal Health agencies including the Centers for Disease Control and Prevention (CDC) and other health officials even post vaccination. There is reason to believe the use of face masks will become a regular component of American lifestyle, as it has become in other parts of the world. This widespread adoption of masks has led health officials to recommended hygiene guidelines for how to properly disinfect worn and contaminated masks.

Most commonly available UVC sanitation devices have not been designed and optimized for the disinfection of face masks. That is, most prior art UVC sanitation devices utilize a "360 degree" sanitation via UVC light source, ranging from bulbs to LEDs, which is not guaranteed to disinfect the entirety of the mask's surface. This is primarily because when a face mask is inserted into the disinfection case, the mask may fold over into a position where the disinfecting UVC light cannot irradiate portions of its surface. This presents a high probability of user misuse which leaves them vulnerable to contaminated "dead zones" located on their mask, where viruses and bacteria are likely to not have been deactivated by the UVC irradiation.

Existing prior art devices specifically aimed at sanitizing face masks rely primarily on gaseous/liquid substances or through-heating elements, which add considerable complexity to the sanitation devices, increasing their size and possibly leading to harmful exposure to vapors if misused. Moreover, heating elements typically consume considerably more energy than low powered UVC LEDs, which have been proven to deactivate viruses quickly and efficiently.

Additionally, none of the currently available systems provide solutions for outer case disinfection. When a user removes a soiled face mask and places it into a sanitation device, they may be inadvertently transferring bacteria and viruses to the outer surface of their device. This leads to contaminated surfaces on the device which may later be inadvertently transferred to the user's face, advancing the spread of illness.

It is within this context that the present invention is provided.

SUMMARY

The present disclosure provides a portable sanitizing device which uses UVC LEDs, configured in a specific pattern and beam angle, to allow for the irradiation of the entirety of a face mask's surfaces. The sanitizing device may be coupled with a specifically designed face mask, manufactured from UV resistant materials, that works in tandem with the sanitation device or may be used with existing reusable cloth masks currently popular in the market. The device may be part of a kit comprising attachment means for affixing it to walls or vehicle interiors, or may be fully integrated with a wall or vehicle interior.

Thus, according to one aspect of the present disclosure there is provided a sanitation device for disinfecting face masks and other items, the device comprising: a container housing with a hinged lid configured to form a closed interior region between a first surface of the container housing and a second surface of the hinged lid; a pair of ear loop fastening elements, each of the pair of ear loop fastening systems including a foldable spring-loaded mechanism moveable between a first position where the fastening elements are distal from one another and one or more second positions where the fastening elements are proximal to one another, wherein in the one or more second positions the elastic tension of the spring-loaded mechanism biases the ear loop fastening elements towards the first position, and thereby being configured to stretch open any face mask installed thereon by providing opposing tension forces to the ear loops of the mask; a first set of UV lamps disposed at one or more positions on the first surface within the interior region and angled to direct illumination towards the second surface of the interior region; and a second set of UV lamps disposed at one or more positions on the second surface within the interior region and angled to direct illumination towards the first surface of the interior region.

In some embodiments, each of the ear loop fastening elements comprises a plurality of hooks and a spring-loaded tension bar, whereby the plurality of hooks and the spring-loaded tension bar operate cooperatively to hold one of a first ear loop or a second ear loop of a face mask, In other embodiments, each of the ear loop fastening elements comprises a pair of moveable wing elements coupled to a central hinge and configured to fold inwards towards one another in response to actuation by a user.

In some embodiments, the sanitizing device will feature a magnetic compartment at its base and can be coupled with a series of magnetic attachment pieces within the sanitizing chamber to allow users to swap interchangeable fixtures designed for numerous high touch items such as (but not limited to) phones, tablets, wallets, credit cards, keys, baby pacifiers, baby bottle tips, and earphones. These fixtures will similarly be designed to ensure items are fixed properly for best surface exposure to the germicidal UV rays within the chamber.

In other embodiments, the magnetic components may be integrated with a mounting system for face masks, the mounting system being permanently affixed within the device interior and comprising magnetic elements configured to couple with such magnetic attachment pieces.

In some embodiments, one of the first set of UV lamps, the second set of UV lamps, or both include UV LEDs.

In some embodiments, the interior region formed by the first and second surfaces comprises one or more reflective surfaces for reflecting UV light emissions from the UV lamps within the interior region.

In some embodiments, the device further comprises a controller and at least one safety sensor configured to detect a change in physical position of the hinged lid with respect to the container housing or an ambient light level above a predefined threshold indicating the hinged lid is not fully forming a closed interior region with the container housing, and, in response to a detection form the at least one safety sensor that the hinged lid is not in a fully close position, the controller is configured to decouple the first set of UV lamps and the second set of UV lamps from a power source.

A user interface and display comprising buttons and lights, or a touchscreen, may also be provided which are electrically coupled to the controller and being configured to receive one or more user inputs for initiating a sanitation cycle, the controller being configured in response to said input to power on the first set of UV lamps, the second set of UV lamps, and to start a timer and cause a time remaining until the end of the sanitation cycle to be displayed.

In some embodiments, the time of each sanitation cycle is stored within a memory accessible by the controller, and containing a number of predefined sanitation cycle settings and associated exposure times for different objects and sanitation intensity levels.

In some embodiments, comprising one or more magnetic elements integrated with the container housing and configured to couple with one or more fixing accessories for holding items to be sanitized in place within the interior region.

According to another aspect of the present disclosure, there is provided a sanitation device for disinfecting a face mask comprising: a tubular container with an interior region, a hinged lid, and an interior tubular wall; a central UV lamp comprising a UV light source within a transparent structure disposed in a central position of the interior region, the central UV lamp having one or more ear loop fastening elements disposed thereon for affixing the ear loops of a face mask wrapped around it in place, and thereby being configured to illuminate a bottom surface of the face mask; and a set of UV lamps disposed on the interior tubular wall and being angled and positioned to illuminate an opposing top surface of the face mask that has been positioned around the central UV lamp.

The central UV lamp may be composed of an inner quartz cylinder with a UVC bulb running through its center. The user then secures the mask around the inner cylinder and connects into a larger outer cylinder lined with UVC LEDs to irradiate the outer surface of the mask. This embodiment may be secured to the rear-view mirror of a moving vehicle.

In both aspects, the device may be integrated with an existing vehicle center console, allowing for future vehicles to come preassembled with a sanitizing compartment for items in case of future pandemics.

In both aspects, the sanitizing device will be sprayed with an external coating of innovative nano-particle technology designed to transform the outer surfaces of the device into an antibacterial surface which can prevent biofilm. Such capability adds an extra layer of prevention against the spread of bacteria, providing effective and long-term antimicrobial protection to the user when disinfecting face masks.

The sterilization device's size will be increased to accommodate sanitizing multiple masks at one time, for family use while inside the home or while traveling.

According to yet another aspect of the present disclosure, a kit is provided comprising the sanitizing device and a mounting kit for those who choose to fix the device near the front door for sanitizing masks as they walk in and out, or securely fastened onto a vehicle dashboard or center console, allowing for a clean compartment to store contaminated face masks and other items for sanitation while driving.

According to yet another aspect of the present disclosure, a kit is provided comprising the sanitizing device and a contactless hand sanitizing dispenser to allow users to sanitize their hands before removing their masks and opening the sanitation case.

BRIEF DESCRIPTION OF THE DRAWINGS

Various embodiments of the invention are disclosed in the following detailed description and accompanying drawings.

FIG. 4B is a perspective view of the device having been cut along line A of FIG. 4A.

FIG. 5B is a perspective view of the device having been cut along line B of FIG. 5A.

Figure 1:
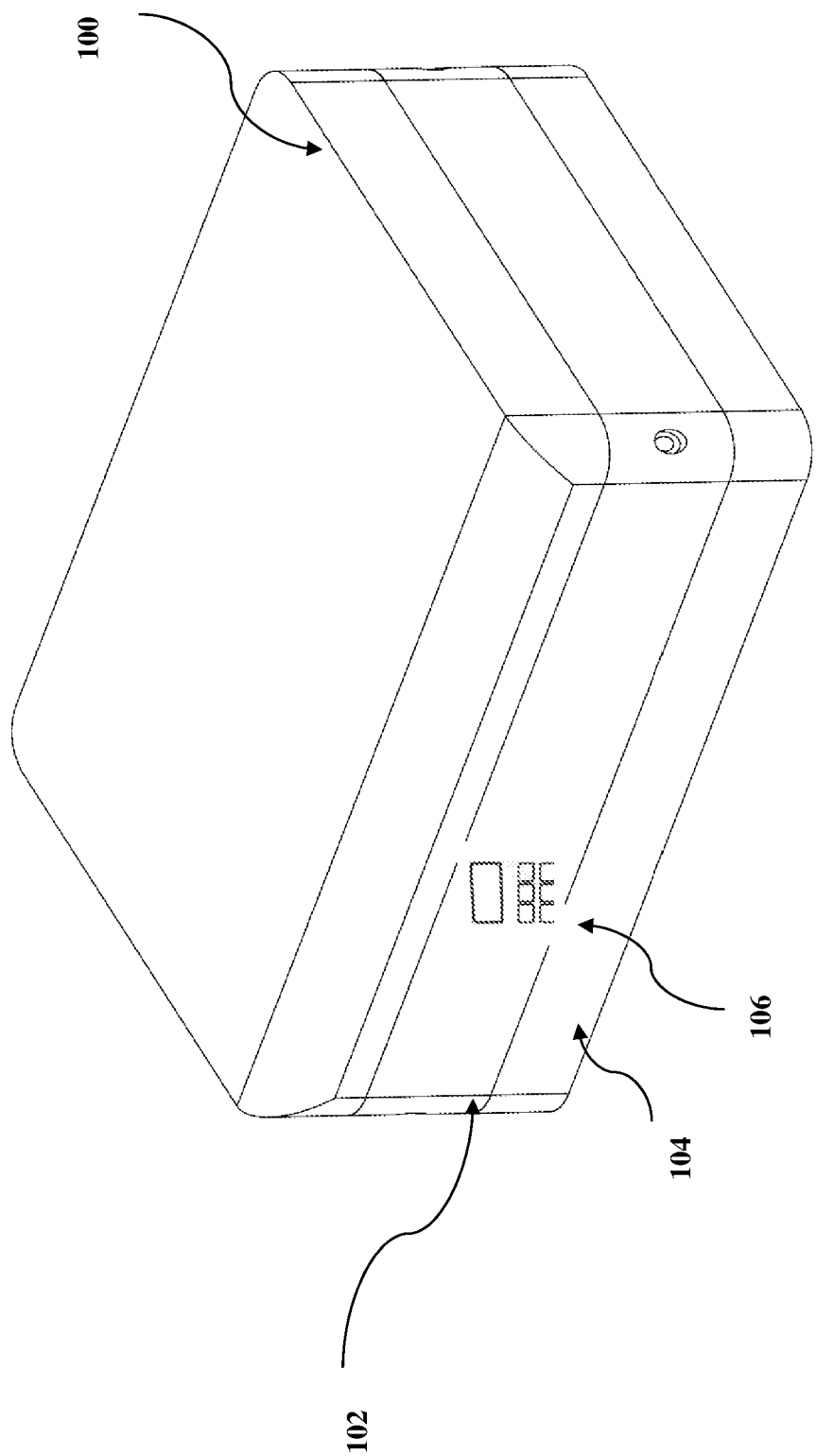
FIG. 1 illustrates a perspective view of a first rectangular embodiment of a sanitation device according to one example configuration of the present disclosure.

Common reference numerals are used throughout the figures and the detailed description to indicate like elements. One skilled in the art will readily recognize that the above figures are examples and that other architectures, modes of operation, orders of operation, and elements/functions can be provided and implemented without departing from the characteristics and features of the invention, as set forth in the claims.

DETAILED DESCRIPTION AND PREFERRED EMBODIMENT

The following is a detailed description of exemplary embodiments to illustrate the principles of the invention. The embodiments are provided to illustrate aspects of the invention, but the invention is not limited to any embodiment. The scope of the invention encompasses numerous alternatives, modifications and equivalent; it is limited only by the claims.

Numerous specific details are set forth in the following description in order to provide a thorough understanding of the invention. However, the invention may be practiced according to the claims without some or all of these specific details. For the purpose of clarity, technical material that is known in the technical fields related to the invention has not been described in detail so that the invention is not unnecessarily obscured.

The terminology used herein is for the purpose of describing particular embodiments only and is not intended to be limiting of the invention. As used herein, the term "and/or" includes any combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

The present invention provides a sanitation device designed for use with various items but which is specifically adapted to sanitize common face masks completely by stretching the mask in a manner that prevents folds, allowing for maximum surface exposure to ultraviolet rays. The device is highly portable and can be operated at home, or while fixed into a vehicle.

Some embodiments of the present invention, including both the rectangular and cylindrical configurations are illustrated below as examples. A third embodiment having an alternative mask mounting system is also illustrated as an example. These embodiment examples should not and are not limited by the illustrations of the accompanying drawings. These embodiments may iterate to include other fastening systems for face masks, include specifically designed face masks to be used in conjunction with the sanitizer device, and may use varying UVC light sources and orientations. Other embodiments may also include varying patterns and shapes, both embossed and debossed, into the inner chamber material, whether coated or uncoated, to achieve varying degrees of optical reflectivity of the UVC light sources.

The term "attachment" is defined as any accessory insert item meant to be coupled with the sanitation device. These attachments are designed to be interchangeable within the UV chamber itself and intent to hold specific equipment for proper sanitation. Some examples include an attachment meant for fixing a face mask within the chamber, an attachment meant to hold a cell phone within the chamber, an attachment meant to hold a user's keys within the chamber, etc. These attachments will be easily swapped by a user via the use of magnetic or mechanical force.

The term "coupled" as used herein, is defined as "connected" although not necessarily directly, and not necessarily mechanically.

The terms "including" and "having" as used herein, are defined as comprising (i.e., open language).

The term "ear loop" is a fastening element that is usually located at opposite ends of the mask. Ear loops are any fabric, cloth, or elastic strap that is intended to be looped over the wearer's ears to fix the mask to the user's face. The definition of ear loops as used throughout this document are inclusive of both one time use elastic type ear loops, singular loops that stretch behind the wearers head instead of over the ears, adjustable ear loops featuring sliding beads, or any other form of reusable cloth ear loops.

The term "mask" is a face covering made of either fiber, gauze, or cloth and intended to fit over the nose and mouth of the wearer to protect against air pollutants, dust, viruses, or bacteria and prevent infection and spread of diseases. The definition of masks as used throughout this document are inclusive of both reusable, washable masks, both woven and nonwoven cloth masks, one time use surgical masks, N95/KN95 type masks, other cone style masks, or any such combination mask that uses a combination of cloth and filter inserts.

The phrase "mask fastener system" is a mechanical or electro-mechanical fastener are inclusive of any such mechanical fixture system which has intended purpose to stretch or fix a face mask into a certain position or orientation for more effective germicidal ultraviolet sanitation. This includes (but is not limited to) systems designed to work with spring loaded mechanical rods, pin and loop mask connections, mask snap fit connections, retaining rings, toggle buttons, zippers, shank buttons, clamped connections, or any other form of button connections intended to fix masks in place.

The term "reflective surface" is defined as any such surface which exhibits the optical properties of bouncing light as per the law of reflection, especially in the UV spectrum. These reflections may be either diffuse reflections associated with textured surfaces or specular reflections associated with smooth surfaces. Optical designers typically use reflective surfaces to optimize the uniformity of radiation dosage within their UV chambers. Reflective surfaces best for UVC purposes are commonly mentioned as (but not limited to) e-PTFE, aluminum plates of various surface finishes, aluminum foil, silver-coatings, gold-coatings, or any such UVC reflective coating applied to interior walls of the UV chamber.

The term "UV lamp" is any light source that emits light in the ultra-violet spectrum. UV lamps are often mercury based. These UV lamps are utilized in a wide array of sterilizing and other functions. Some examples include, but not limited to, handheld UV lamps, benchtop UV lamps, UV bulbs, UV tubes, UV viewing cabinets, horticultural grow lamps, etc.

The term "UV LED" are typically compact light-emitting diodes (LED) that produce smaller quantity of ultraviolet light. For sterilization purposes, these LEDs fall mainly into the UVC spectrum, being defined as a light wavelength of between 200 nm to 280 nm on the electromagnetic spectrum.

The present disclosure relates to a novel, sterilizing case device for carrying and disinfecting reusable face masks, for use both in a portable manner as well as fastened within a vehicle. More particularly, the invention relates to a new design that ensures masks are positioned in a flat and stretched orientation, ensuring an even distribution of disinfecting UVC irradiation to the entirety of the mask's surface. The device further comprises means for affixing other types of items in place during a sanitation cycle. Thereby, the present invention solves the problems of the related art detailed previously.

The invention allows for the proper disinfection of face masks on your person, or within your vehicle, without the need to return home for a laundry cycle. The invention achieves this via a novel mask attachment device that fits most standard reusable cloth masks in popular circulation as of this writing.

Various example embodiments of the device are provided herein, but each embodiment comprises a mask-mounting system configured to hold a mask in an unfolded position and an interior surface of the case which is highly reflective to maximize the sanitation effect of the UV LEDs in the interior.

Figure 3:
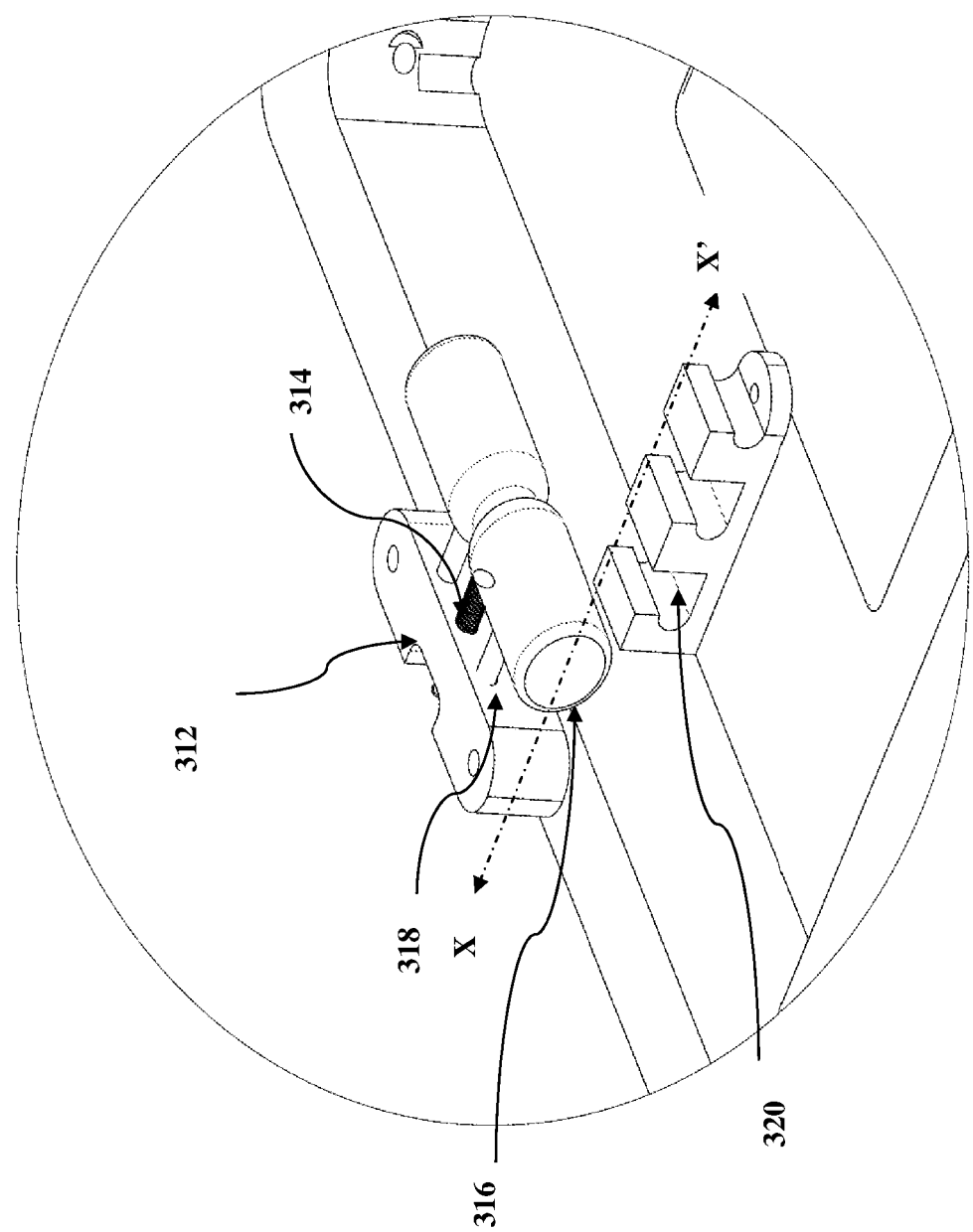
FIG. 3 illustrates a close-up view of the mechanical fastening system used to ensure the mask's surfaces are fully exposed to the ultraviolet irradiation, according to one example configuration of the present disclosure.

In one example, a two-piece, spring loaded fixture in the case interior is provided that connects to the ear loops of the mask. One piece, shown in FIG. 3, incorporates three separate slits, spaced at half inch increments from one another to accommodate Small (S), Medium (M), and Large (L) face masks. Although half inch increments are shown, other distances are within the true scope of the present invention. This piece is disposed on the lower level of the device and is used as a hold to fix the ends of the mask in place. The second piece, shown also in FIG. 3 is a mechanical spring device under tension, where the mask is looped around and pulled towards the other end of the device, connecting the mask to both ends of the fastening device. This effectively removes the slack from the mask, ensuring even irradiation along its surface.

In another embodiment, this same effect may be achieved by a similar pair of fasteners on the ends of the case which are not spring loaded. Each fastener resembles the first piece of the previous embodiment and incorporates three separate slits, spaced at half inch increments from one another to accommodate S, M, and L face masks. User will manually hook ear loops into the slit correlating with their mask size.

In another embodiment, this same effect may be achieved by a pair of mechanical small pegs on the ends of the case. In this embodiment, our portable UVC mask sanitizer will be coupled with a specially designed face mask meant to be used with the device. This custom face mask may include small holes sewn into the fabric of the ear loops to be connected over the mechanical pegs. Each correlating sized face mask will have holes sewn into the correct position on the ear loops to effectively stretch the face mask when coupled with the pegs.

The device may utilize low energy consumption UVC LEDs to achieve a portable sanitization effect. UVC LEDs with wavelengths ranging from 270-280 nm are preferred due to relatively high sanitation effect while simultaneously more economic than similar shorter wavelength LEDs.

The device utilizes a novel light ray reflectivity system to scatter the light emitting from the UVC diodes in multiple directions within the case. In some examples the device utilizes a thin plate manufactured from a high reflectivity material such as polished aluminum or any other such substrate treated with a reflectivity coating or paint. This reflectivity plate may further be embossed or stamped with varying shaped cavities to reflect light more evenly via a dimpled surface.

As generally known in the art, a polished surface may reflect photons by the law of reflection which states that as a light ray reflects off the smooth surface, the angle of incidence will equal the angle of reflection. In contrast a dimpled surface allows for the light to bounce in many directions, providing a more even distribution of the UV irradiation and will generate fewer hot spots. This even distribution of light reduces the overall number of reflections needed for the UV light ray to reach the mask's surface. As every reflection leads to inherent energy loss, shortening the photons pathway to the masks surface will improve overall efficiency in the system. This helps achieve a more 360-degree sanitation effect, ensuring face masks are irradiated at various angles from light rays emanating from all LEDs within the case.

By coupling the face mask fastening device with the reflective lining, the invention achieves higher sanitation effects on face masks compared to generally known products from the prior art, which do not ensure entirety of a mask's surface has been irradiated during the disinfection cycle.

The present disclosure of the given embodiments should be considered as only an exemplification of the invention and is not intended to limit the invention to these specific embodiments as illustrated by the figures or the descriptions below.

The present invention will now be exemplified using three example embodiments: a first rectangular embodiment, a second cylindrical embodiment, and a third embodiment having an alternative design for mounting masks.

FIG. 1 depicts the first embodiment of the sanitation device, shown in a completely closed position and ready to begin sanitation. The hinged lid 100 is attached to the middle body 102 of the sanitation device via mechanical hinges (not shown). The hinged lid 100 is designed to be opened and closed by the user, triggering safety sensors, such as photo-sensors, or contact switches, or non-contact switches activated by the opening of the lid 100. These safety sensors help prevent the user from exposure to UVC irradiation while device is open, and as soon as any one of the sensors detects an indication that the device has been opened during a sanitation cycle, a controller of the device is configured to shut off power to the UV LEDs. The middle body 102 is further mechanically attached to the bottom piece 104, which will house most of the sanitation device's electronics and control circuits. In one example the sanitation device includes a digital interface 106 to communicate when sanitation is active, time left to sanitize, and once sanitation has completed, that the lid is safe to reopen.

Figure 2A:
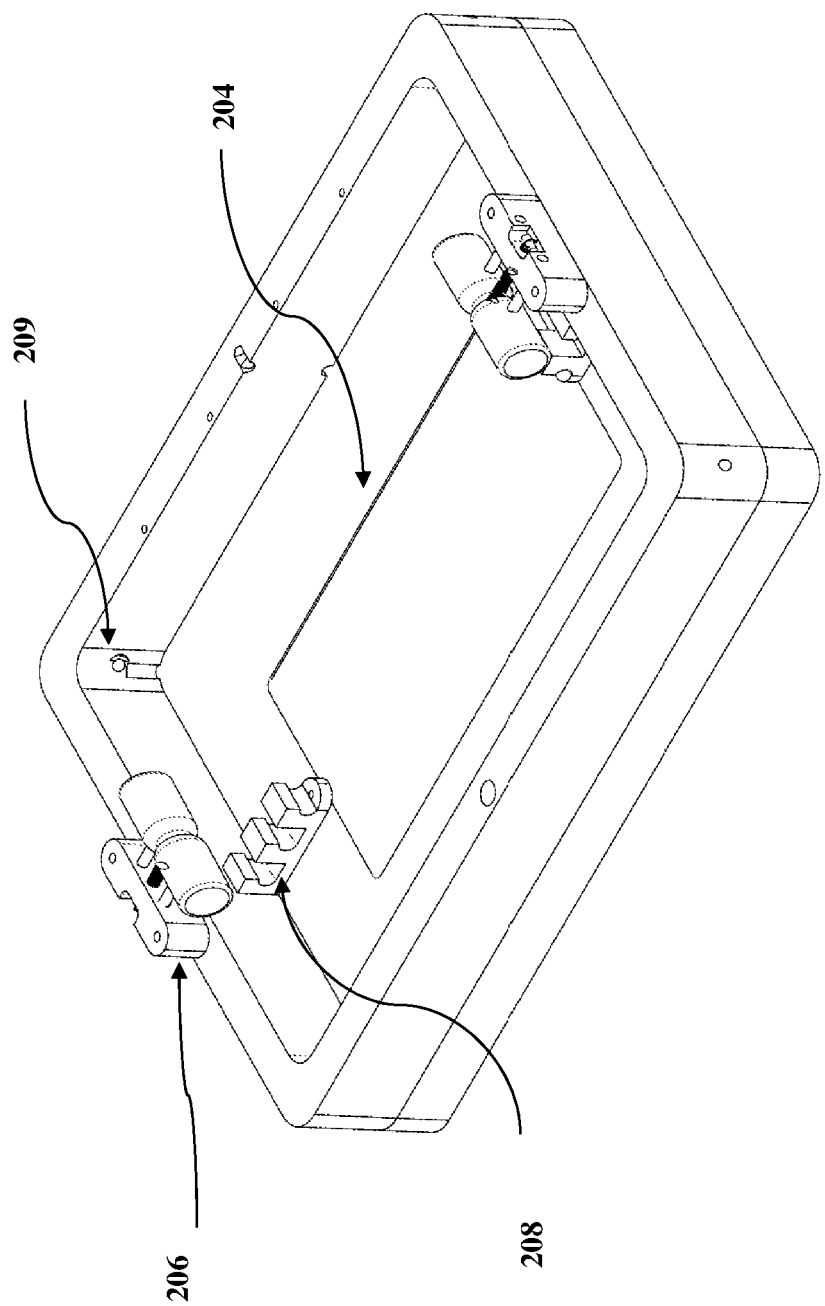
FIG. 2A illustrates a perspective view of the first embodiment of the sanitation device, shown with the lid open to detail the inner cavity and UVC LED arrangement, according to one example configuration of the present disclosure.

FIG. 2A depicts the first rectangular embodiment of the sanitation device, shown with the lid open to detail the inner chamber 204. This is where the face mask 250, or other items in need of sanitizing, will be placed before beginning the sanitation cycle. On the sides of the sanitation device, both pieces of the ear loop fastening systems of the face mask 250 are detailed. The first piece 206 includes a spring compression system or spring-loaded tension bar 316 (shown in FIG. 3) to stretch the face mask's fabric. The second mask mounting component 208 includes a plurality of hooks that will catch the ear loop of the face mask are detailed on the bottom surface of the sanitation device. Used in tandem, this system will secure the face mask 250 in place, prevent folds, and supply sufficient surface tension to stretch the fabric for maximum exposure to the UVC light. The inner components of this sanitation device are discussed in more detail in FIG. 3. Pilot hole 209 depicts the fastening location for one of the multiple UVC LEDs.

Figure 2B:
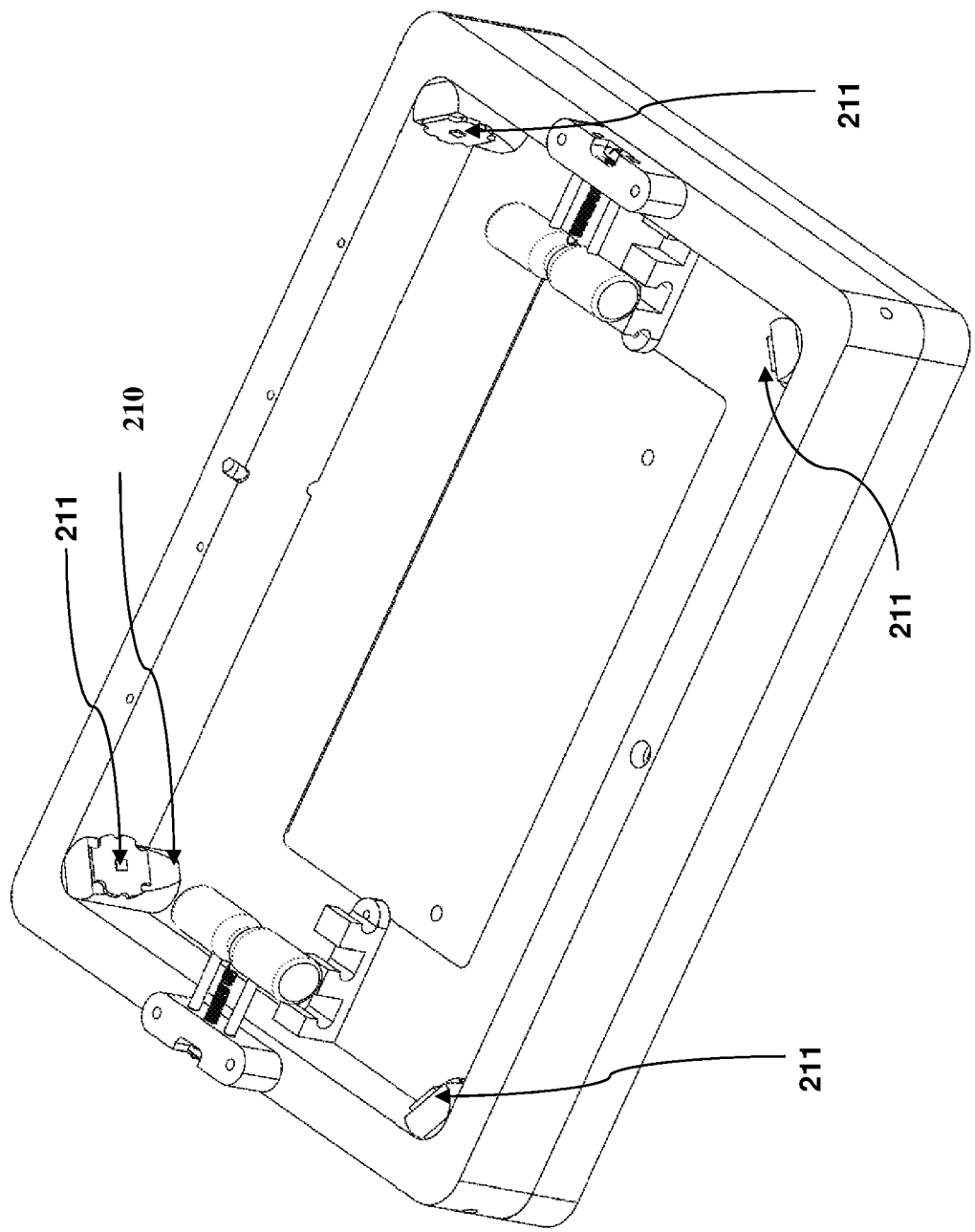
FIG. 2B illustrates a perspective view of the first embodiment of the sanitation device, shown with UVC LEDs and corresponding angled mounts fastened into the assembly, according to one example configuration of the present disclosure.

FIG. 2B depicts the first embodiment of the sanitation device, shown with the UVC LED optical components 211 and corresponding heat sinks 210 mounted on the pilot holes 209 at each corner of the device.

Figure 2C:
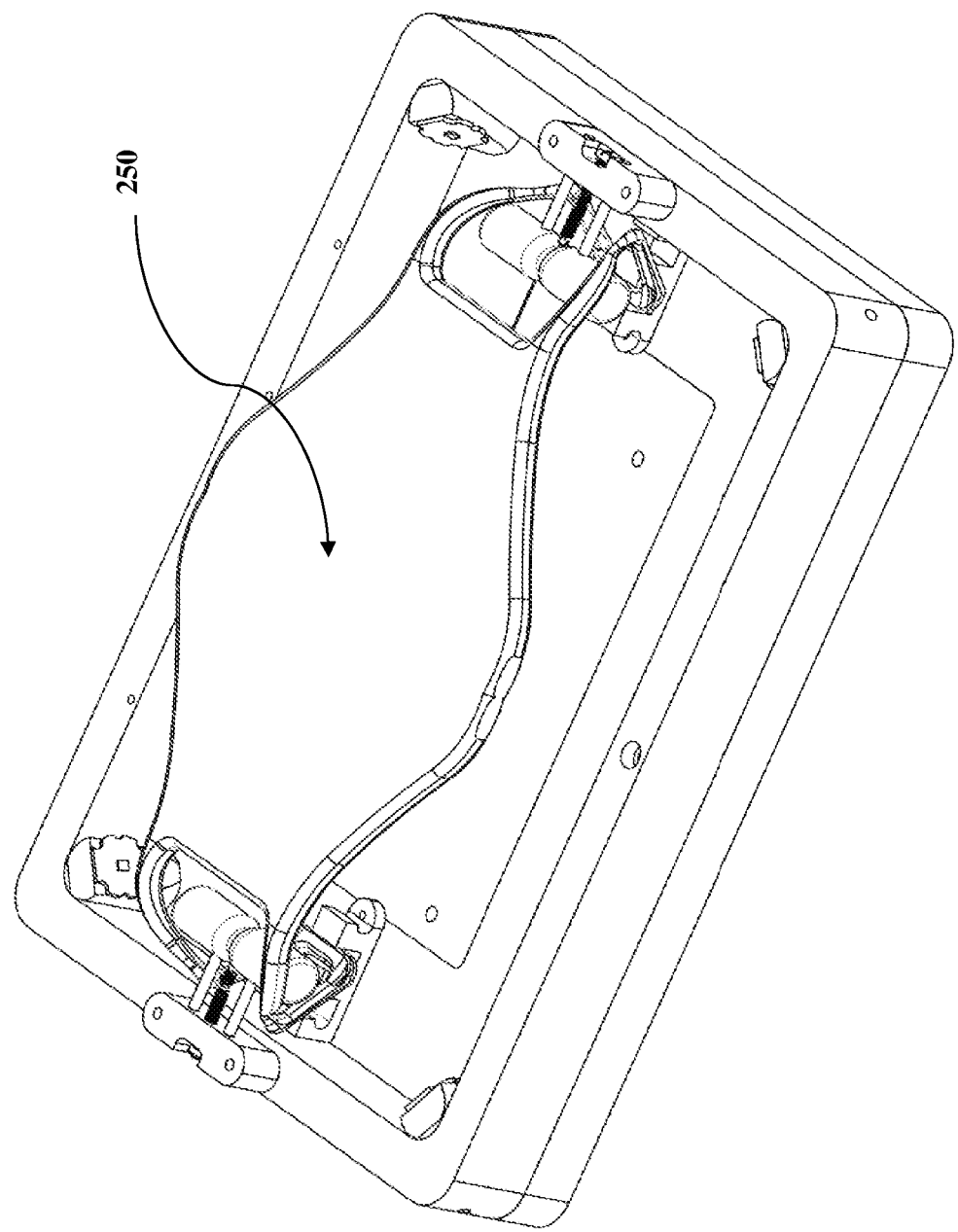
FIG. 2C illustrates a perspective view of the first embodiment of the sanitation device, shown with an example mask securely fastened via the mechanical fastening system, according to one example configuration of the present disclosure.

FIG. 2C depicts the first embodiment of the sanitation device with a mask 250 fully fastened into the system and ready for disinfection. The mask is shown mounted in its stretched state, with a clear flat surface, devoid of any shadows, folds, or crannies that would otherwise prevent effect sanitation.

FIG. 3 depicts a close view of the mechanical fixture system of FIG. 2A. The top piece consists of a mechanical base 312, which is fastened to the main body of the sanitation device 102 as shown and anchors the piece. Spring 314 is mechanically attached to tension bar 316 and will be manually extended by the user when hooking in the mask's opposite ear loops. Mechanical rods 318 serve as guide pieces to constrain the lateral movements of the spring assembly to one dimensional movement along the line X-X' as shown. The hook piece 320 is shown fastened to the bottom of the sanitation device and will serve as the "catch" to anchor the ear loops 252 while stretching. The combination of the hook piece 320 and the tension bar 316 work cooperatively to hold the ear hook 252 of a face mask 250 taut as shown in FIG. 5B using opposing tension on each of the ear loops of the face mask. These components may be shifted and altered as necessary to maximize compatibility with as many varying types of face masks commonly found in circulation. In another example, this system may be altered slightly to reflect the sanitation device's coupling with a custom designed face mask for fastening. These changes may include a small hook to catch the loops on one side while the opposite side stretches the mask via spring extension.

Figure 4A:
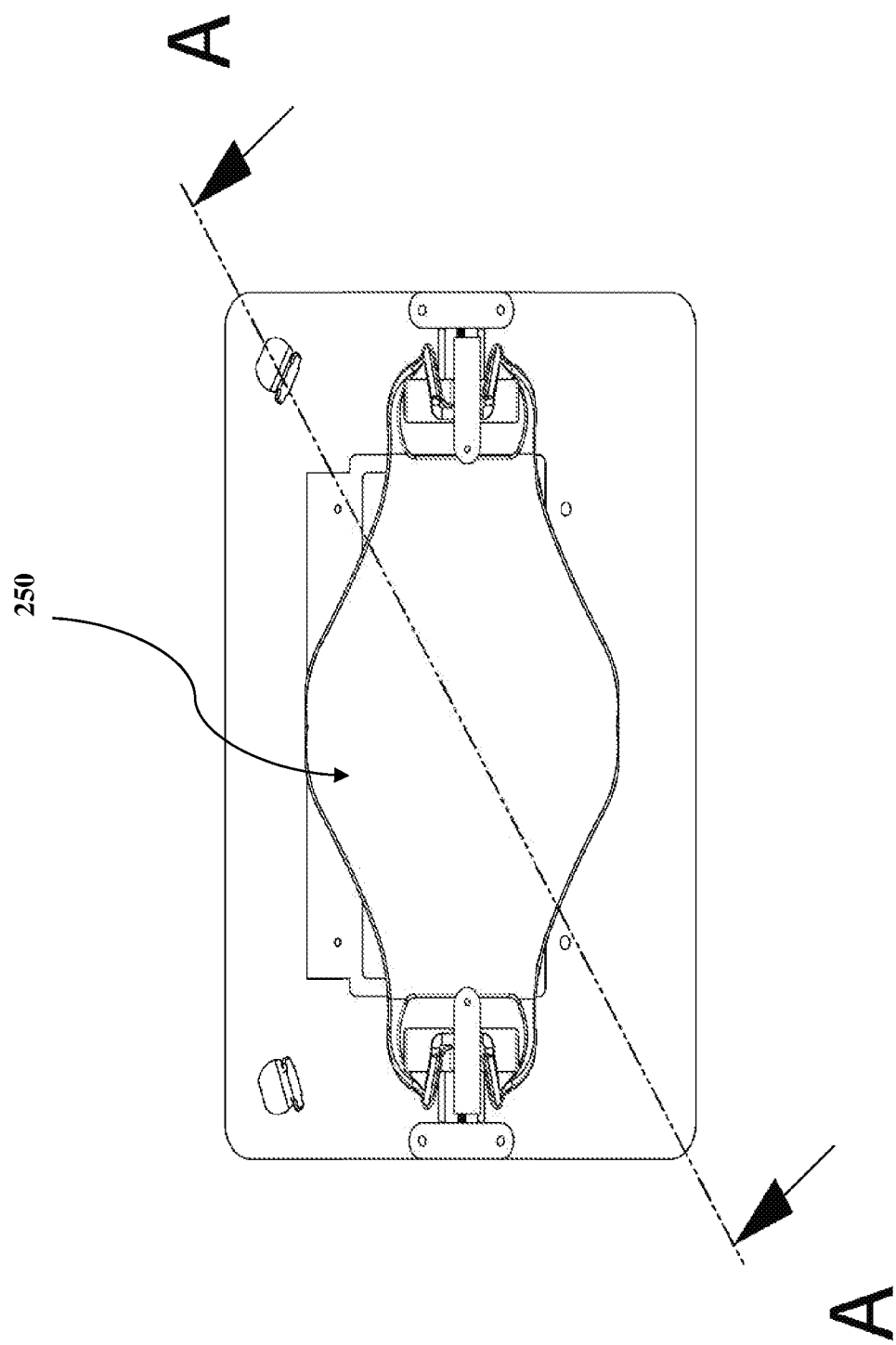
FIG. 4A and FIG. 4B illustrate two segments of a sectional view of the first embodiment of the device cut laterally to show the bottom angles within the device while in operation, according to one example configuration of the present disclosure. Specifically.
Figure 4B:
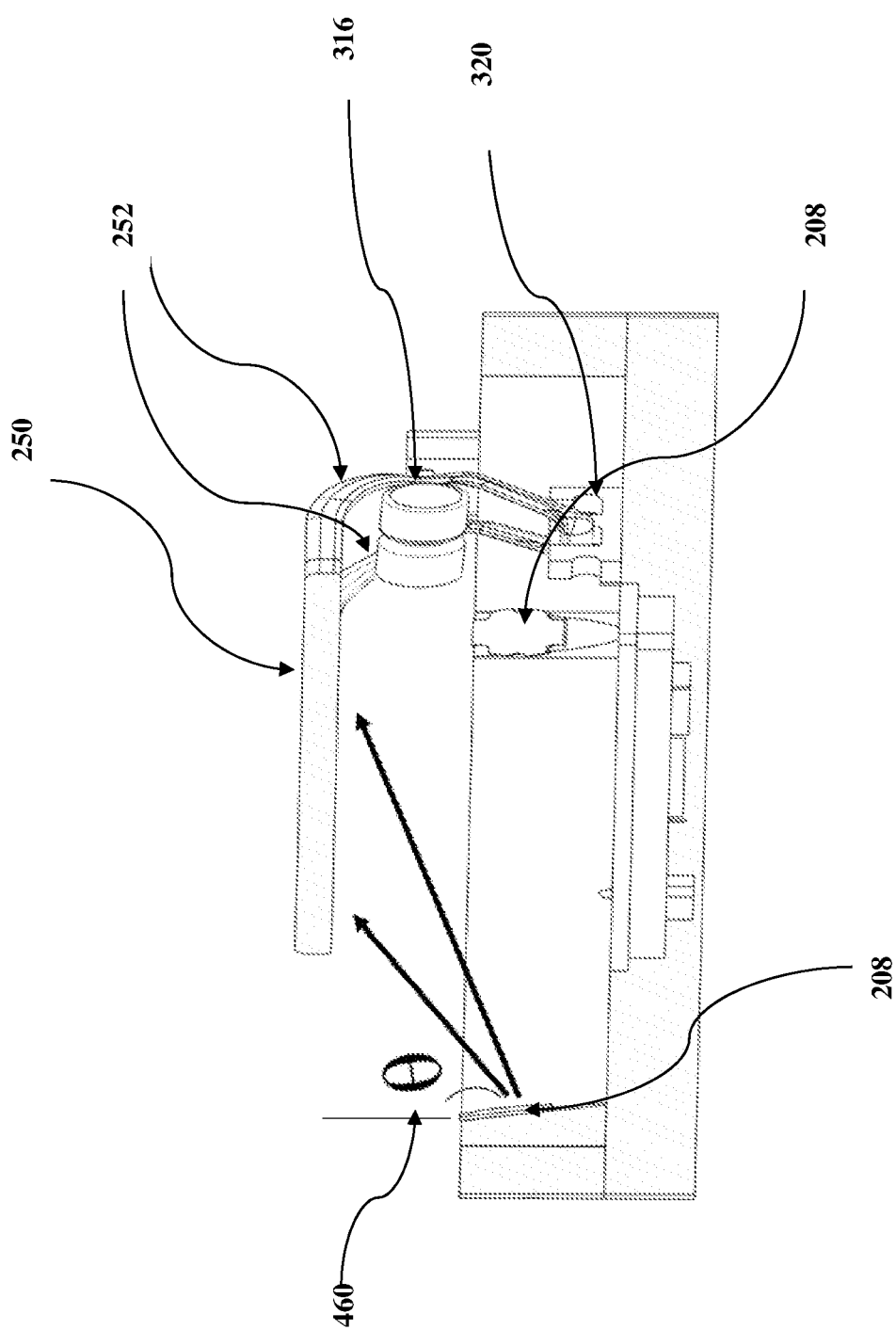

FIG. 4A and FIG. 4B depicts a sectional view of the first embodiment of the sanitation device. In these figures we are showing the lower portion of the lateral cut along line A-A, to highlight the angled nature of the designed LED mounts. The lower set of LEDs irradiate via UV illumination the inner side of the face mask. The LED mounts are fixed to the outer housing and feature an angled surface with respect to the vertical normal, specified in FIG. 4B as theta 460 to tilt the multiple light rays emanating from the LED, covering a wider viewing angle of the mask. Theta has been nominally set to about 30 degrees, but other ranges of the sanitation device may range this angle from 15 degrees through 60 degrees.

Figure 5A:
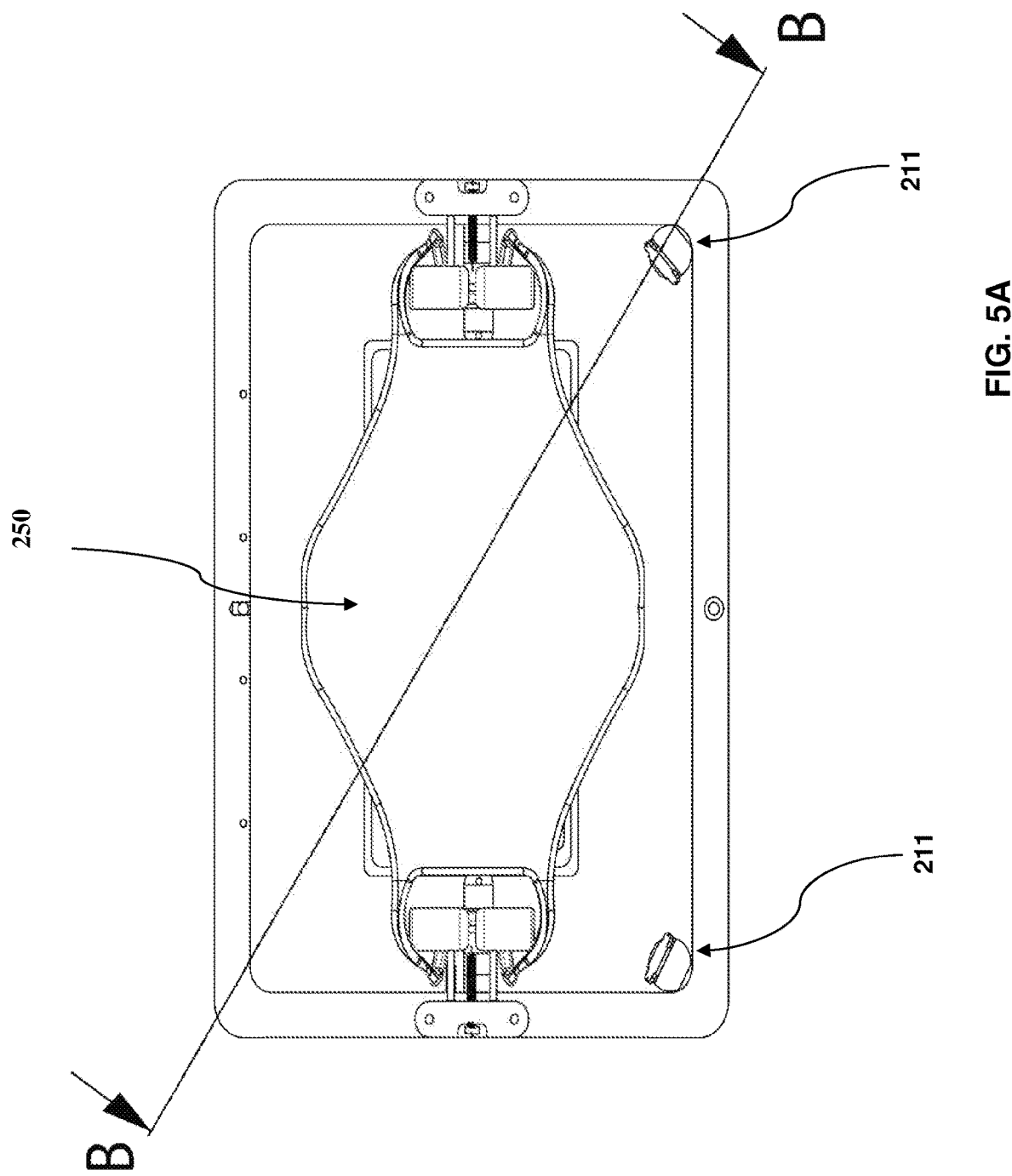
FIG. 5A and FIG. 5B illustrate two segments of a sectional view of the first embodiment of the device cut laterally to show the bottom angles within the device while in operation, according to one example configuration of the present disclosure. Specifically.
Figure 5B:
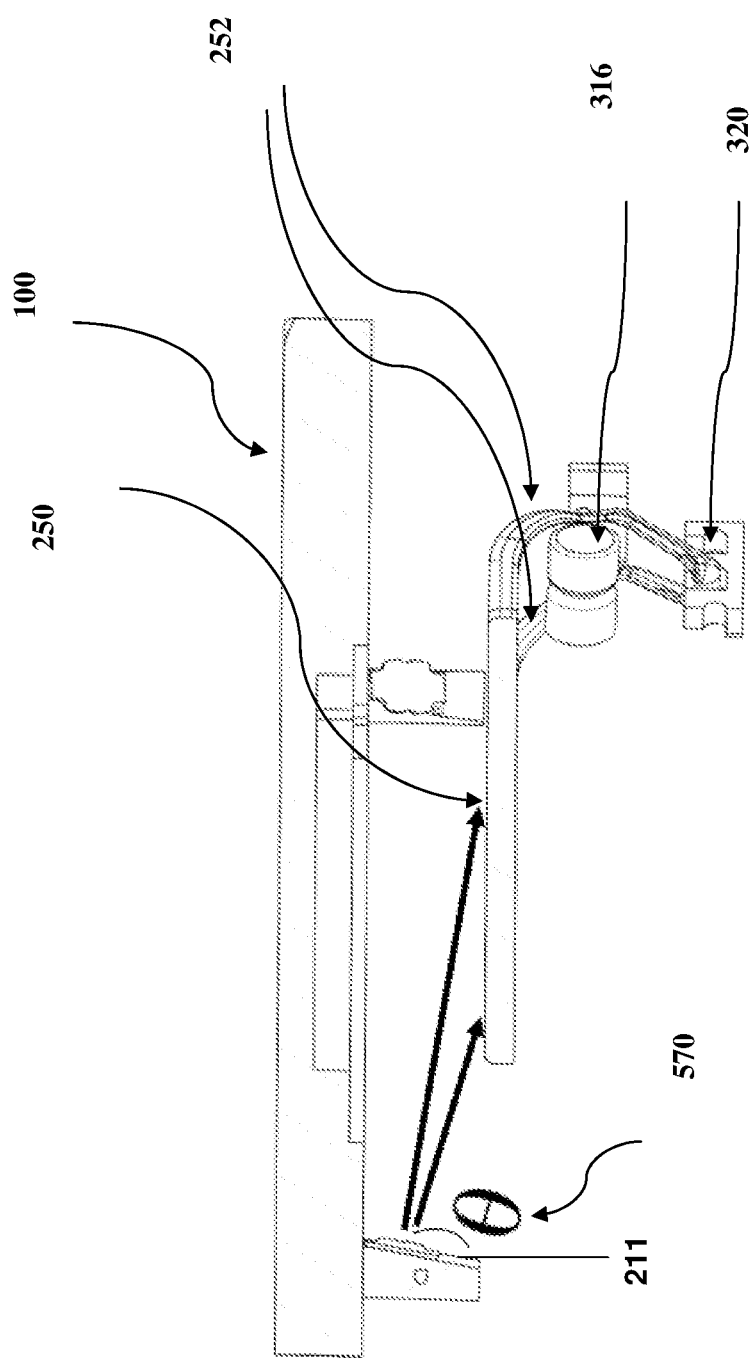

FIG. 5A and FIG. 5B depicts a sectional view of the sanitation device, shown in the rectangular configuration. In these figures we are showing the upper portion of the lateral cut along line B-B, to highlight the angled nature of the designed LED mounts. The upper set of LEDs irradiate through UV illumination the outer side of the face mask. The LED mounts are fixed to the outer housing and feature an angled surface with respect to the vertical normal, specified in FIG. 5B as theta 570 to tilt the multiple UV light rays emanating from the LED, covering a wider viewing angle of the face mask. Theta has been nominally set to about 30 degrees, but other examples of the sanitation device may range this angle from 15 degrees through 60 degrees.

Figure 6A:
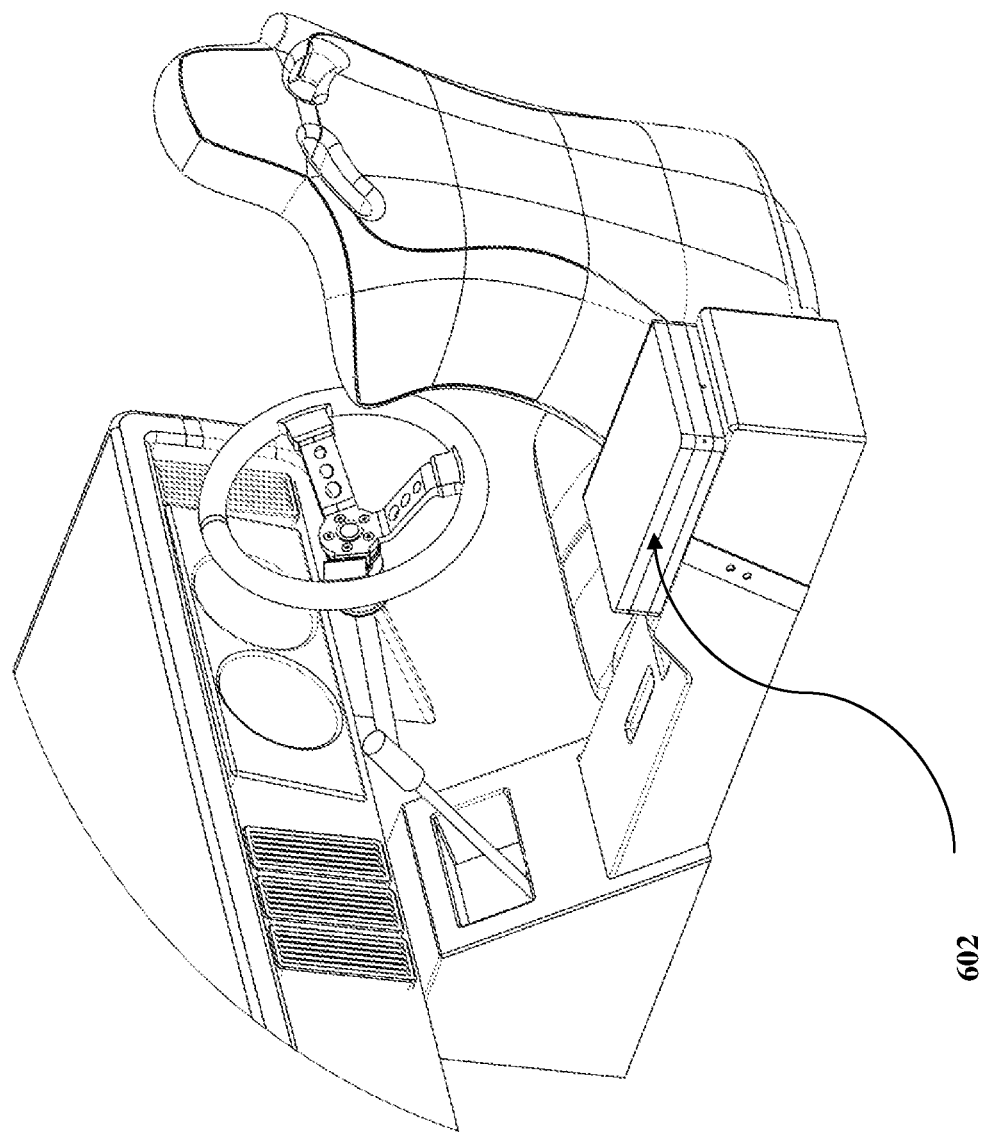
FIG. 6A illustrates a perspective view of the first embodiment of the device, fastened within a vehicle for easy disinfection while driving, according to one example configuration of the present disclosure.
Figure 6B:
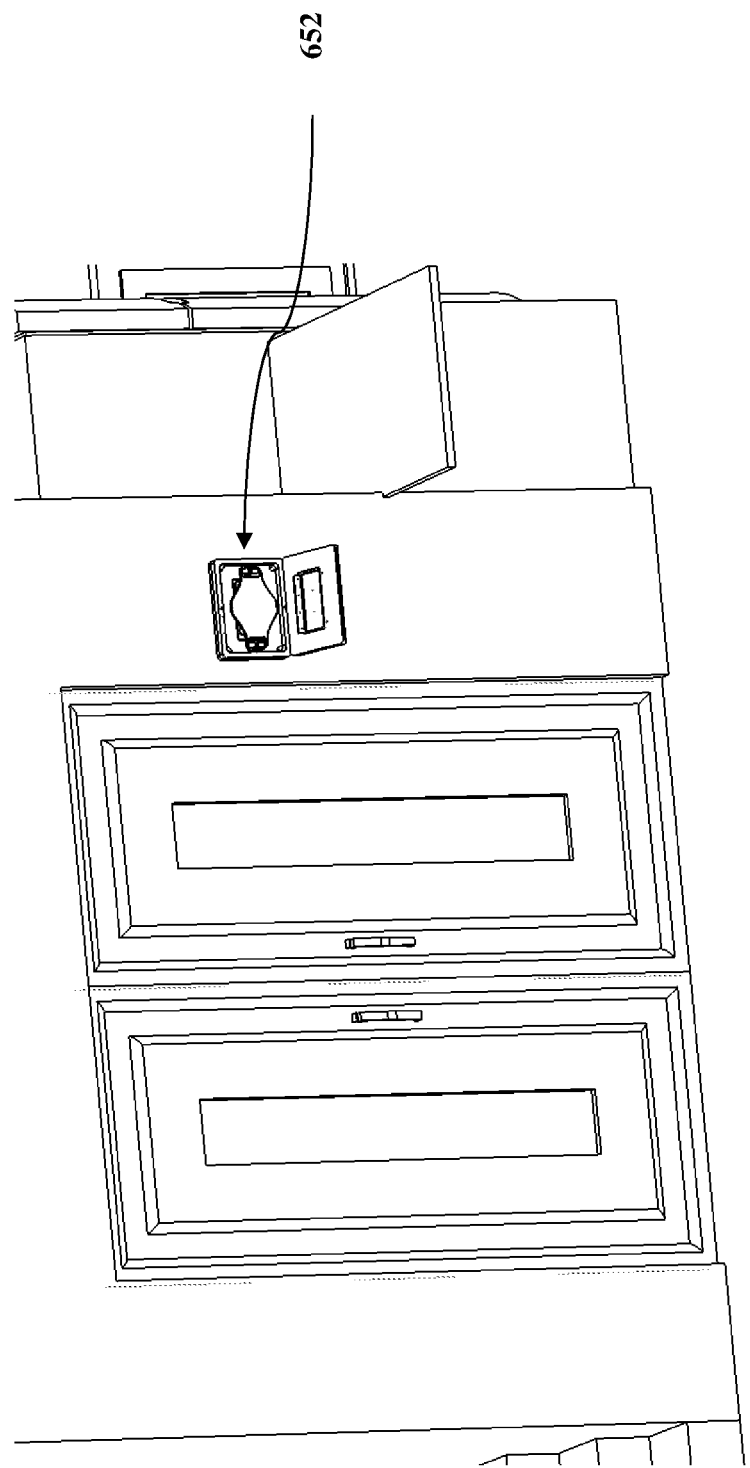
FIG. 6B illustrates a perspective view of the first embodiment of the device, fastened onto a wall for at home use through an included wall mounting kit, according to one example configuration of the present disclosure.

FIG. 6A depicts the sanitation device, shown in the rectangular configuration 602 securely fastened within a moving vehicle via an attachable strap system connected to the center console, ensuring the sanitation device is secure. This ensures safe operation even while driving. In another embodiment the sanitation device may be strapped into the glove compartment or attached via high strength suction cups to the dashboard or within the trunk. These and other attachment means may be provided alongside the device itself as a kit FIG. 6B depicts the sanitation device, shown in the rectangular configuration, securely fastened to the wall of a home for those which prefer a fixed location. We intend to include a wall mount system with the sanitation device 652. In other embodiments of the sanitation device may be expanded in size to allow for simultaneous cleaning of multiple masks in similar fashion, allowing entire families to walk in and immediately place their masks within a clean sanitation chamber.

Figure 7:
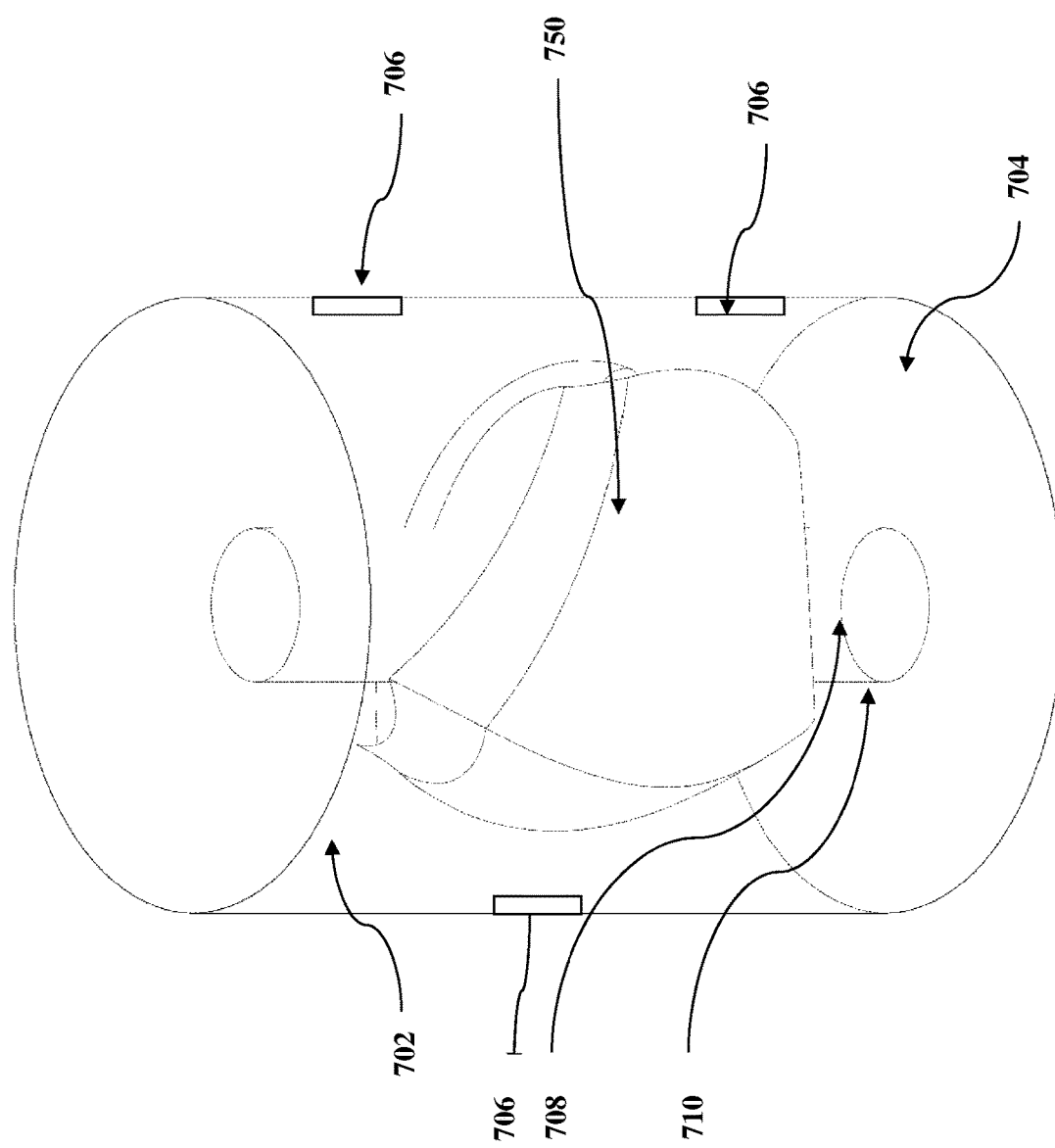
FIG. 7 illustrates a perspective view of a second cylindrical embodiment of the sanitation device, according to one example configuration of the present disclosure.

FIG. 7 depicts a second alternative embodiment of the sanitation device with a cylindrical outer housing, 702. Within the housing, runs a vertical UVC central or cylindrical lamp 708, encased within a clear cylindrical quartz housing 710 in an axial position within the sanitation device as shown. A hinged lid or bottom of the outer housing 702 is attached via mechanical hinges (not shown) to form an enclosed chamber for sanitation. This allows for the user to open the container and slide the internal component with the quartz cylinder out of the sanitation device. The face mask 750 is then wrapped around the cylindrical quartz housing 710 in the interior space of the sanitation device as shown and hooked together on the back end via a mechanical fastener for the ear loops, such as a clip, clasp, or hook (not shown). Once the mask has been secured, the user then slides the inner component back into the housing and closes a hinged lid 704. The inside of the outer housing 702 is also lined with multiple UVC LEDs in order to irradiate the outer surface of the face mask as well as the inside surface via the UVC lamp 706. The inner surface of the outer housing 702 in one example includes a reflective surface or coating. This design takes advantage of the cylindrical curve utilized by common face masks in circulation to reduce overall size of the sanitation device.

Figure 8:
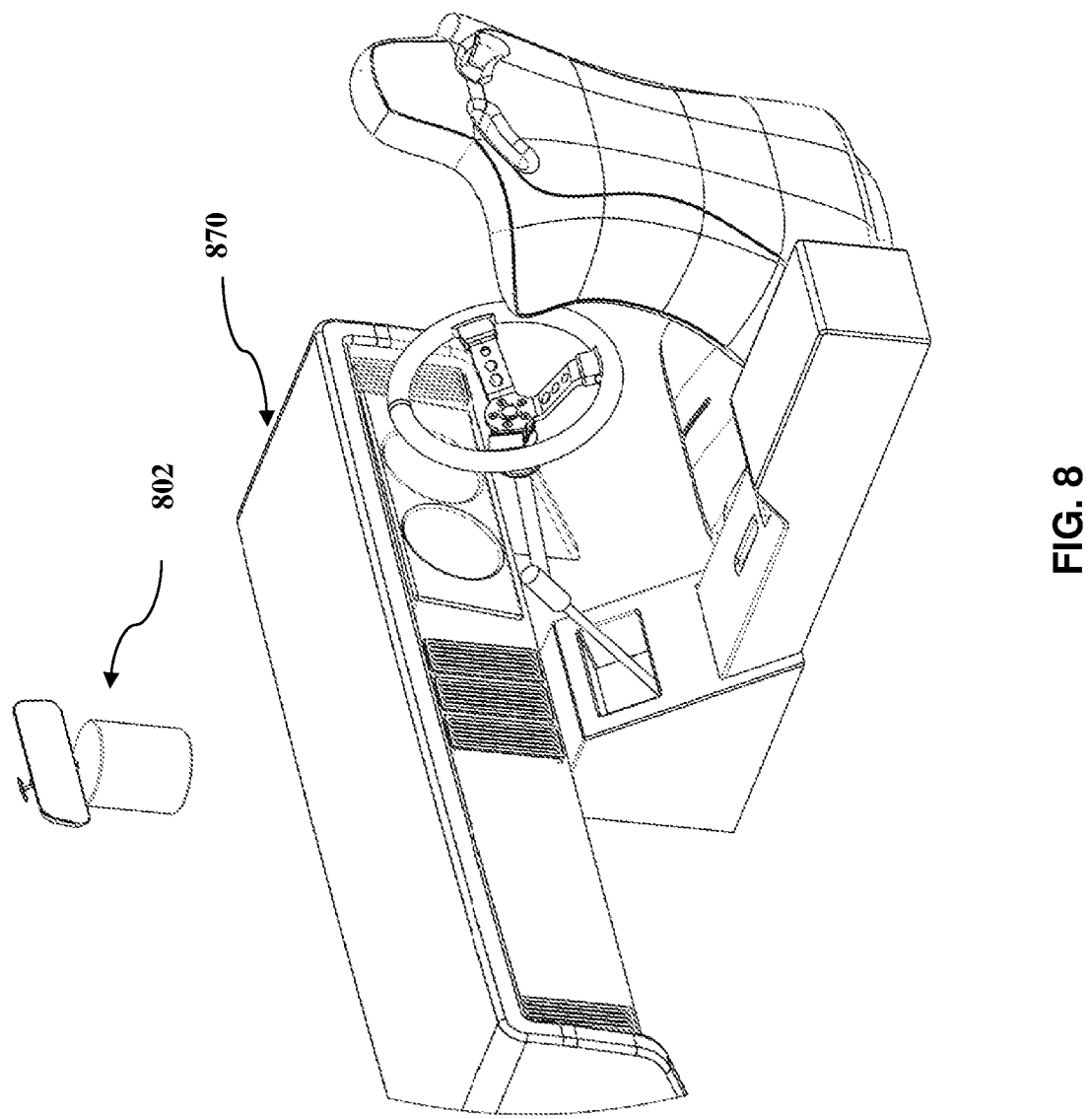
FIG. 8 illustrates a perspective view of the second cylindrical embodiment of the device fastened within a vehicle for easy disinfection while driving, according to one example configuration of the present disclosure.

FIG. 8 depicts the sanitation device, shown in the cylindrical configuration 802 securely fastened within a moving vehicle 870 via an attachable mechanical connection hook system that is fastened to the rear-view mirror, ensuring the sanitation device is secure. This ensures safe operation even while driving. Future embodiments may have this sanitation device fastened into the cup holder or center console of the moving vehicle.

In all embodiments, the device is equipped with a controller, for example a microcontroller unit (MCU) on an integrated PCB board, that has firmware and custom logic preprogrammed into it to allow a user to easily select and initiate one or more sanitation cycle options. The circuitry also includes a power source and switches to control each of the UV lamps. A user interface 106 includes lights for providing status and one or more buttons for a user to begin a sanitation cycle. Alternatively, the interface may be a touchscreen. A count down time display is implemented in response to the user starting the sanitization cycle and all the safety sensors being satisfied.

Each preprogrammed sanitation cycle will have a respective built-in exposure time. For example, different sanitation cycle exposure times may be associated with different items and at different speeds—a user may be able to choose an item they are sanitizing, i.e. a phone, and then select a level at which they would like the sanitation cycle to be performed, i.e. recommended, high intensity, low intensity, etc. The exposure times for each type of item at each setting may be stored in a memory of the controller and selectable via the touchscreen interface of the device.

When a sanitation setting is selected and the device case is closed, the controller may be further configured with one or more fail safe mechanisms to ensure that a user is not exposed to UV radiation during the cycle by opening the device prematurely or dropping it etc.

Figure 9:
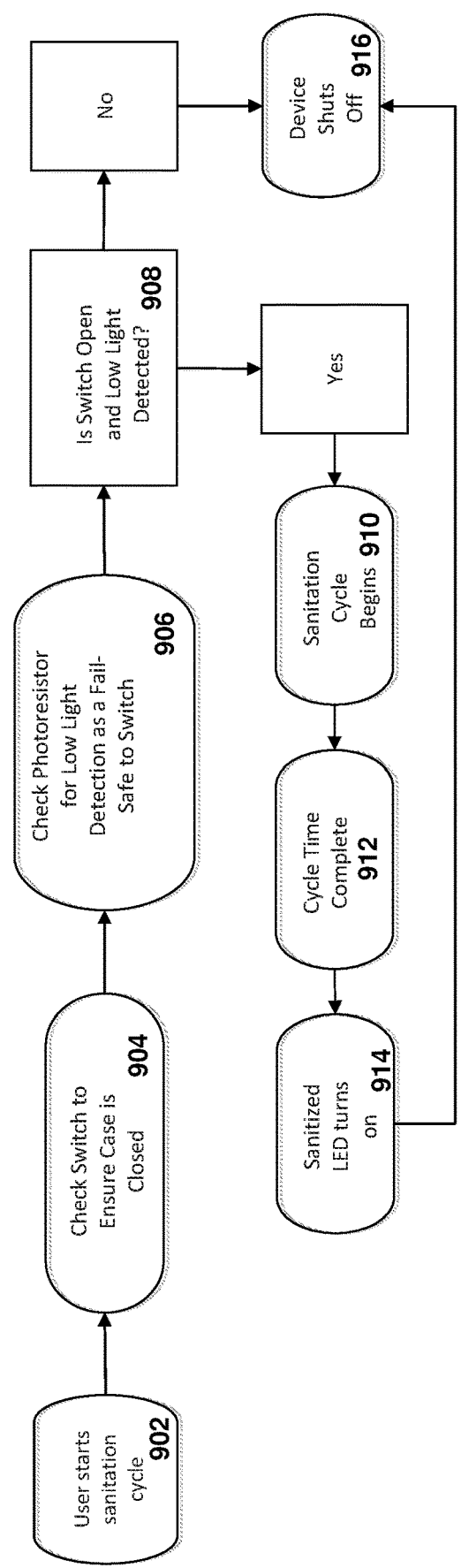
FIG. 9 illustrates a flow chart of the operations of a controller during a sanitation cycle.

FIG. 9 is a flow chart showing an example sequence of operations performed by a controller of the device according to the present disclosure during a sanitation cycle. In a first step 902 the user selects and start the sanitation cycle via the interface. In a second step 904 the controller checks a physical snap switch, which is embedded in the lid and detects physical compression against the base of the device to ensures the lid has been properly closed. In a third step 906 the controller checks a photocell resistor in the device interior which is configured for low light detection. In a fourth step 908 the controller checks the detected light level against a threshold and determines that the light level is acceptable and that the snap switch has not been triggered. In a fifth step 910 the controller powers on the LEDs for the full length of the sanitation cycle and a timer will appear on the touch screen. Once the timer reaches zero the sanitation cycle is complete and the device will power down the LEDs in a sixth step 912. In an eighth/continuous step 914 performed throughout the process the controller will continue to check if the two conditions are broken, and if they are the PCB will shut off power to the UVC LEDs 916 to ensure no harmful exposure to the user by mistake.

Figure 10:
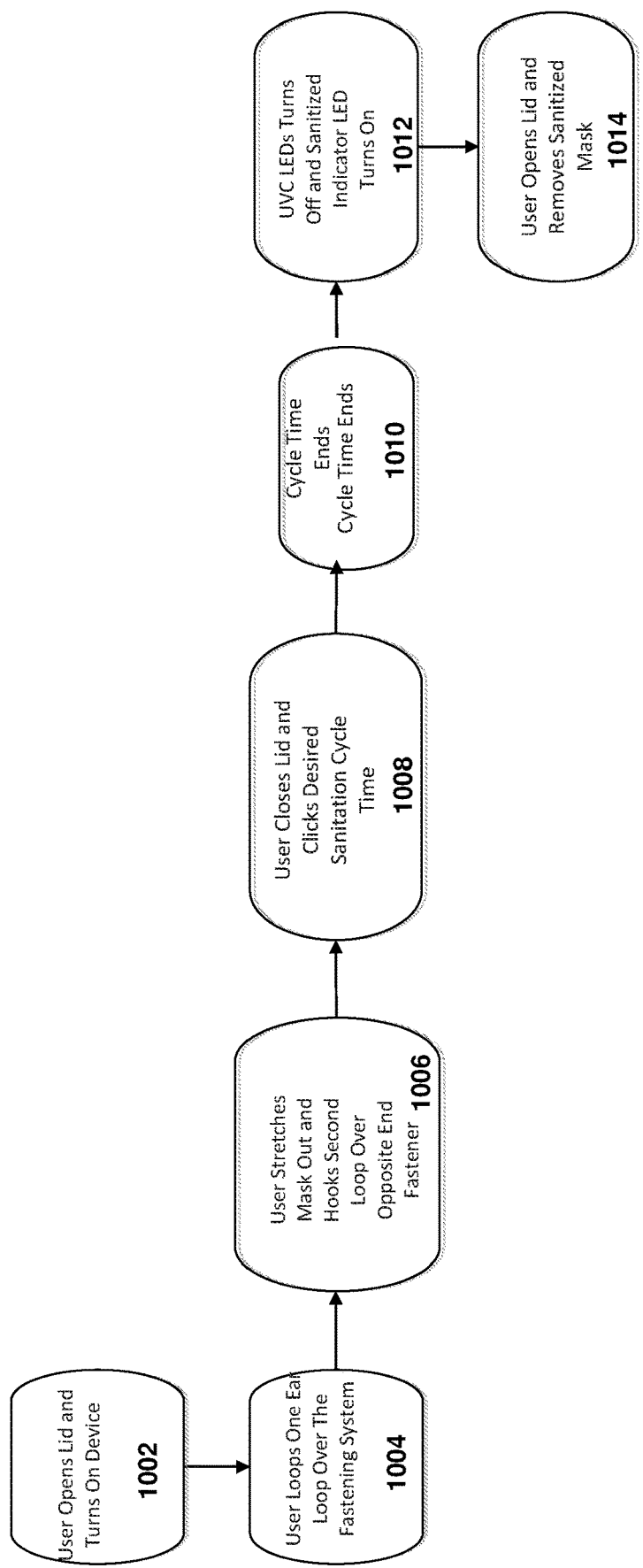
FIG. 10 illustrates a flow chart of the operations of a user during a sanitation cycle.

FIG. 10 is a flow chart showing an example sequence of operations of a user during such a sanitation cycle for sanitizing a mask. The user begins by opening the lid of the case and turning the device on 1002. The user then loops one ear loop of the mask over the ear fastening system 1004. The user then stretches the mask out and hooks the opposing ear loop of the mask over the ear fastening system on the opposing end of the device interior 1006, this flattens out any creases and folds that may have been present in the mask. The user then closes the lid and, using the interface of the device, selects a desired sanitation cycle program or sets a specific time 1008, this will start the display timer countdown. Once the countdown display reaches zero, the cycle will end 1010 and the LEDs will power down, indicated to the user by the indicator LEDs on the display changing 1012. The cycle is now finished, and the user can open the case lid and remove the sanitized mask 1014.

Figure 11A:
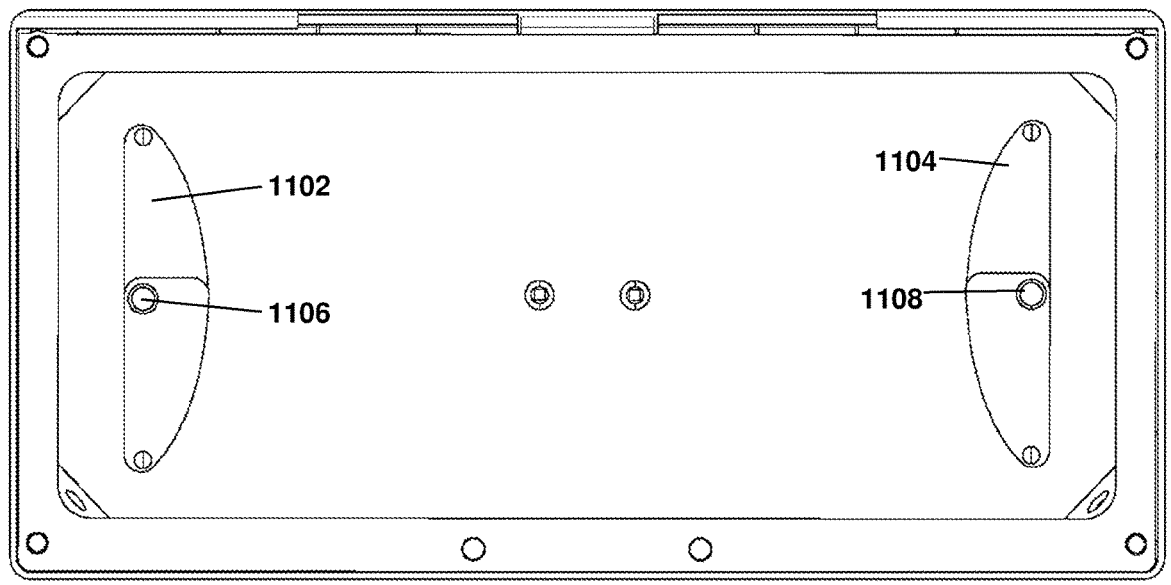
FIG. 11A and FIG. 11B illustrate top-down views of the interior of a third embodiment of the sanitation device according to the present disclosure, the third embodiment comprising an alternative mounting system for face masks.
Figure 11B:
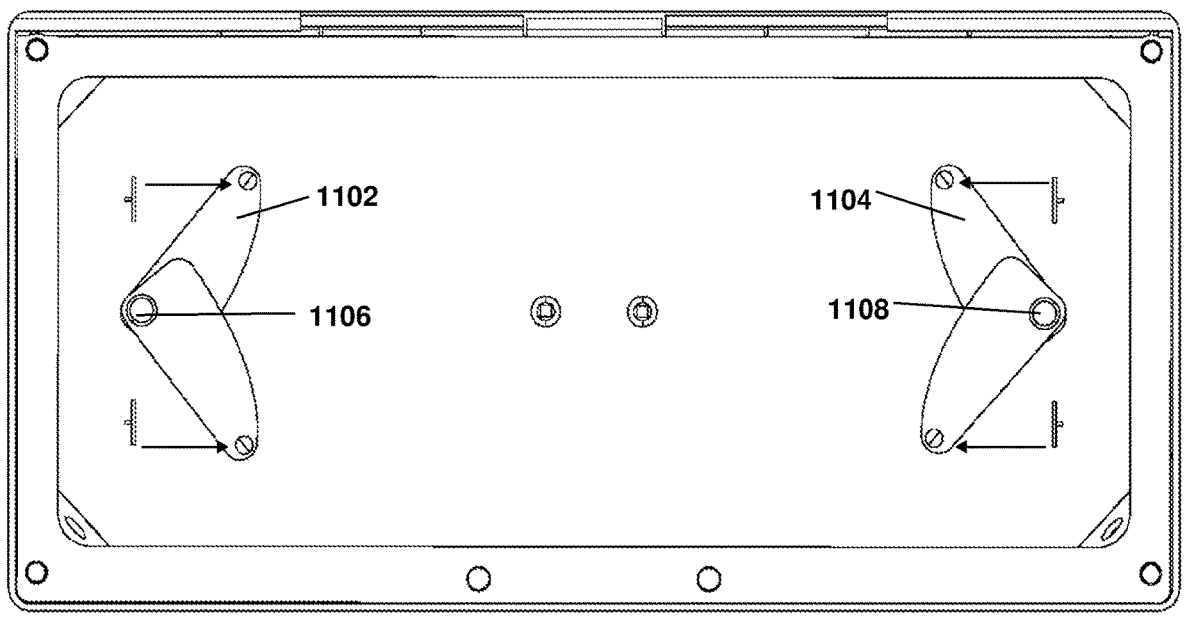

FIG. 11A and FIG. 11B are top-down views of the interior of a third embodiment of the sanitation device according to the present disclosure, the third embodiment comprising an alternative mounting system for face masks and a set of magnetized elements for coupling with position fixing accessories.

In the illustrated example, a spring-loaded wing system is used for ensuring a mask mounted within the apparatus is stretched out to expose a maximum amount of surface area to the UV light elements in the interior region during sanitation cycles. The spring-loaded wing elements 1102 and 1104 are each disposed about a central hinge 1106 and 1108 and are configured to fold inwards towards the center of the interior region under pressure, with the spring force of the mechanism biasing them back to the position shown in FIG. 11A to keep any mask mounted thereon as taut as possible during the cycle. This should allow for light stretching to reduce folds and creases, a key blocker for UVC sanitation efficacy.

Figure 12:
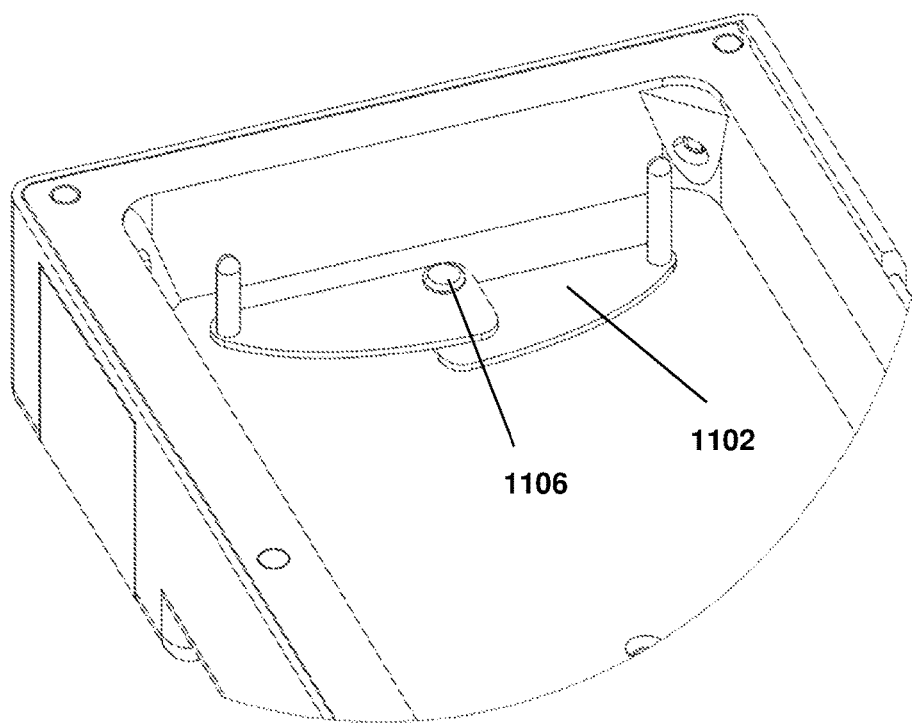
FIG. 12 illustrates a perspective view of an interior portion of the third embodiment of sanitation device and a close-up of the alternative mask mounting system.
Figure 13:
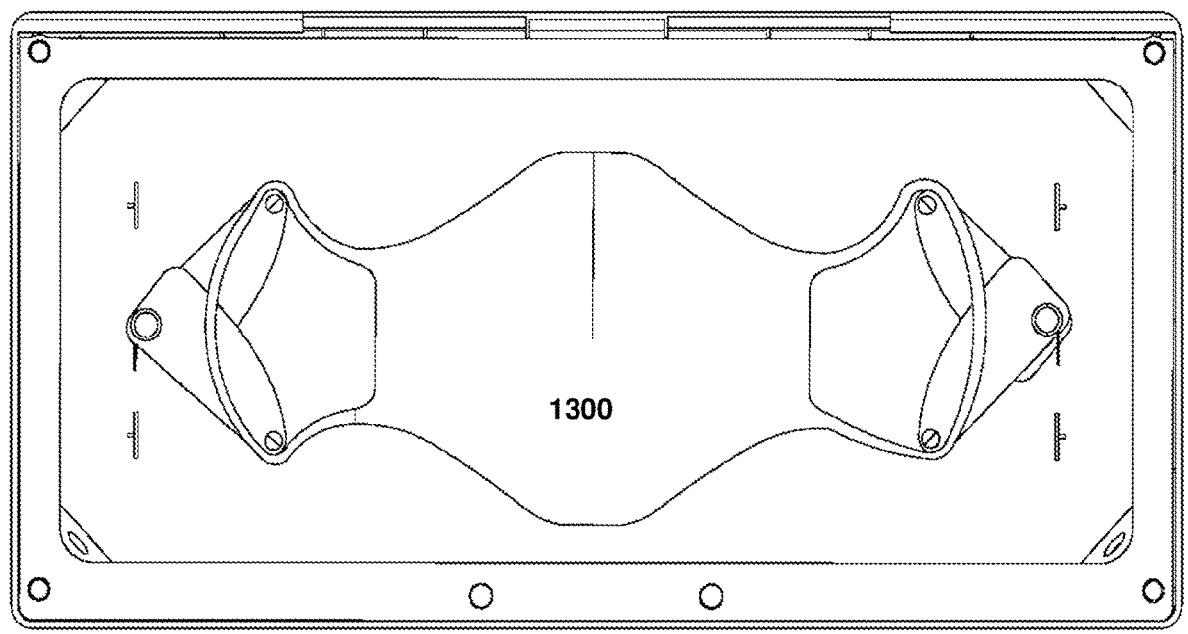
FIG. 13 illustrates a top-down view of an example mask mounted in the interior of the third embodiment of the device of the present disclosure.

FIG. 12 is a perspective view of an interior portion of the third embodiment with a close-up of the foldable wing mask mounting system. FIG. 13 is a top-down view of an example mask 1300 mounted in the interior region of the third embodiment of the device.

Figure 14A:
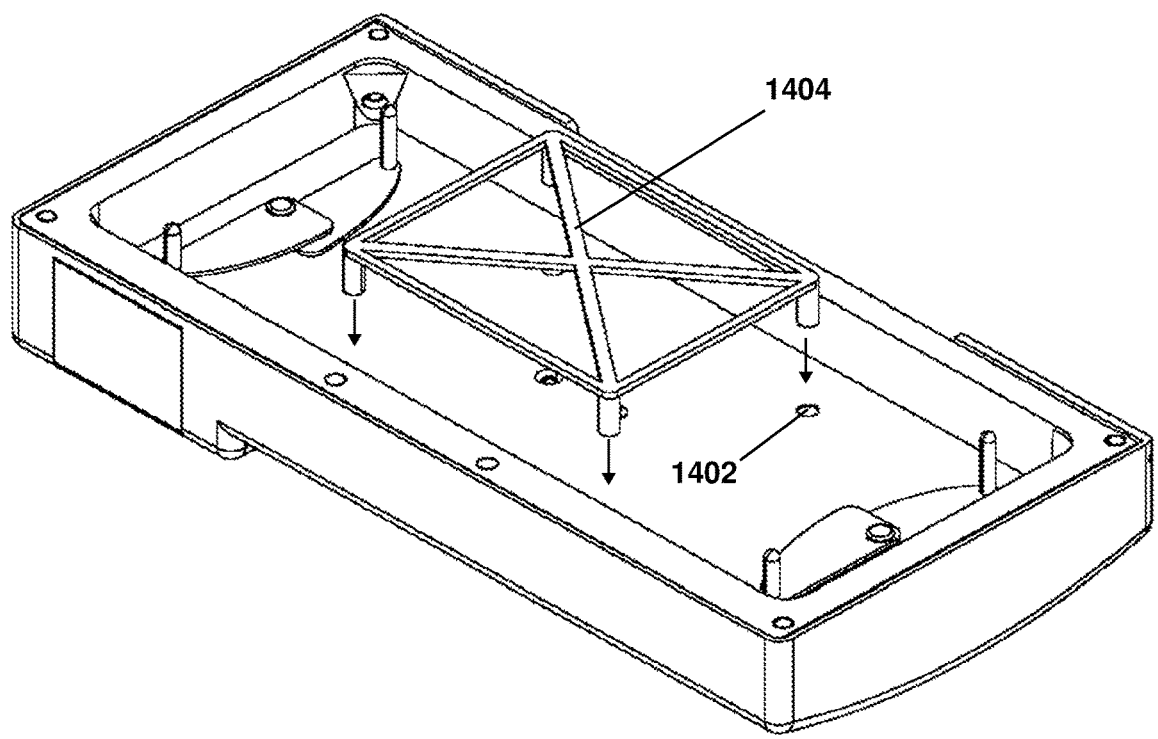
FIG. 14A and FIG. 14B illustrate perspective views of the third embodiment of the device with a set of magnetic mounting points on the base of the interior being used to couple a fixing element in place to properly old one or more items in place.
Figure 14B:
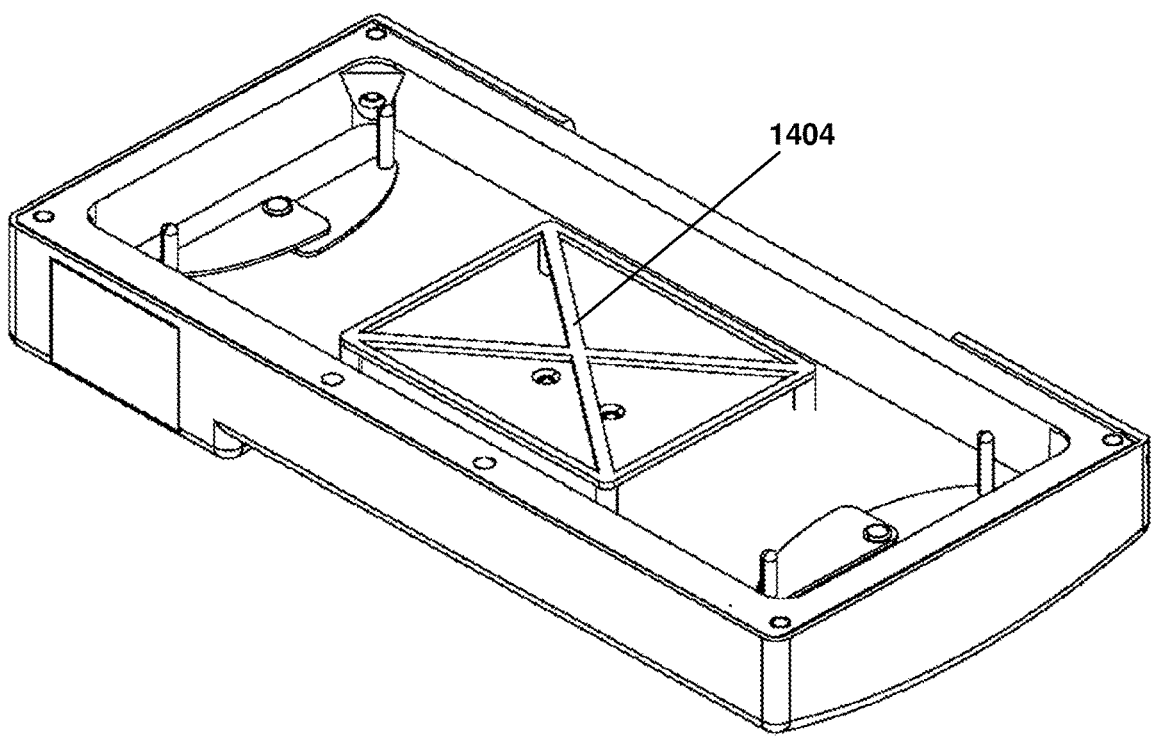

FIG. 14A and FIG. 14B are perspective views of the third embodiment of the device with a set of magnetic mounting points 1402 on the base of the interior region being used to couple a fixing element 1404 in place to properly hold one or more accessory items in place during sanitation cycles such as pens, phones, baby products, and other everyday high-touch items that would not be held in place by the mask fastening system. In the example configuration shown there are four magnetic mounting points 1404 at the bottom of the base to allow for quickly popping in an assortment of different attachments to accommodate items of different shapes and sizes—these attachments may be provided as part of a kit with the device.

Alternatively, the magnetic wing elements 1102 and 1104 may themselves have integrated magnetized elements to allow for larger drop in attachments to be placed over them within the interior region so that they sit over the wing fastening system in its rest position.

The attachment pieces like element 1404 may in some examples be made from quartz or another material highly transparent to UV radiation to facilitate high UV transmission during the sanitation process.

Figure 15:
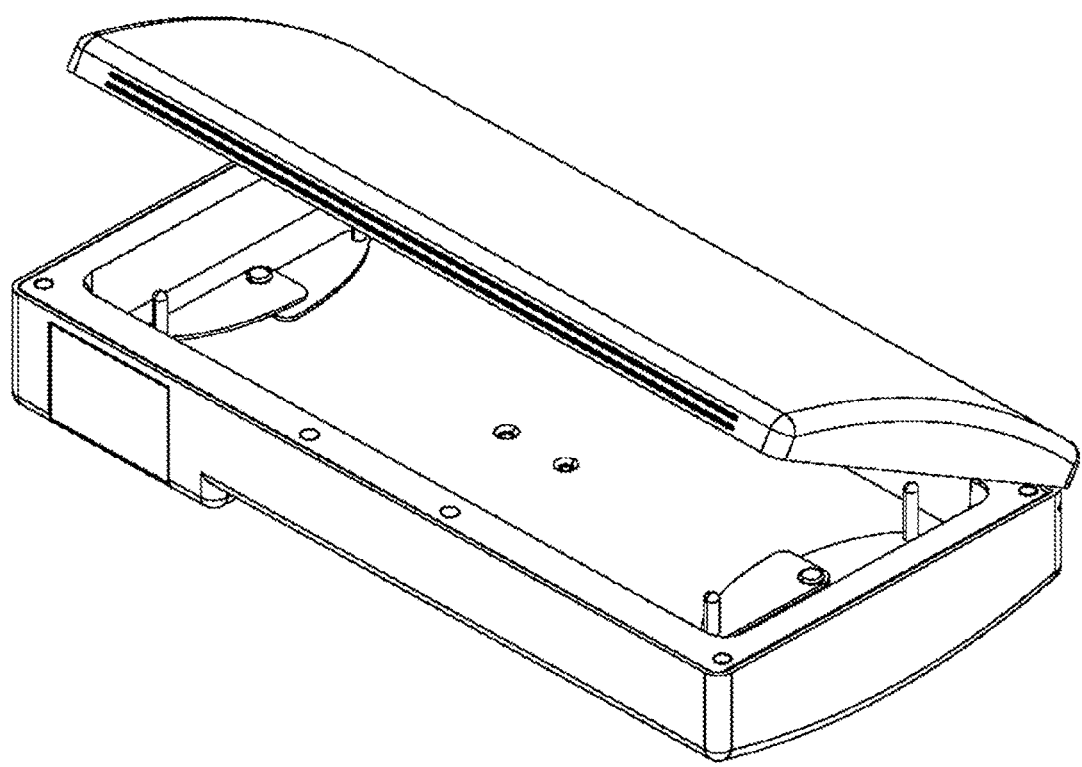
FIG. 15 illustrates a perspective view of the third embodiment of the device with the lid attached, but open to expose the interior of the device.
Figure 16:
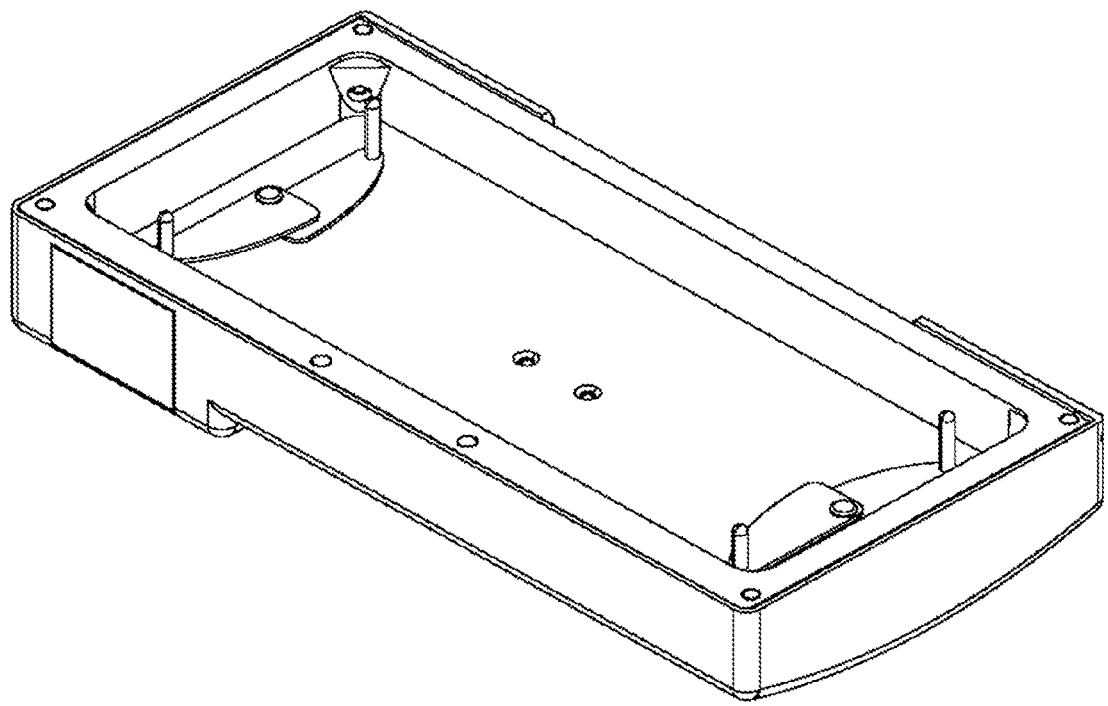
FIG. 16 illustrates a final perspective view of the third embodiment of the device in the same position as FIG. 15 but with the lid removed.

FIG. 15 and FIG. 16 are perspective views of the third embodiment of the device with the lid attached (FIG. 15) and removed (FIG. 16).

Unless otherwise defined, all terms (including technical terms) used herein have the same meaning as commonly understood by one having ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

The disclosed embodiments are illustrative, not restrictive. While specific configurations of the sanitation device and attachment kits have been described in a specific manner referring to the illustrated embodiments, it is understood that the present invention can be applied to a wide variety of solutions which fit within the scope and spirit of the claims. There are many alternative ways of implementing the invention.

It is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. A sanitation device for disinfecting face masks and other items, the device comprising:
   a container housing with a hinged lid configured to form a closed interior region between a first surface of the container housing and a second surface of the hinged lid;
   a pair of ear loop fastening elements, each of the pair of ear loop fastening systems including a foldable spring-loaded mechanism moveable between a first position where the fastening elements are distal from one another and one or more second positions where the fastening elements are proximal to one another, wherein in the one or more second positions the elastic tension of the spring-loaded mechanism biases the ear loop fastening elements towards the first position, and thereby being configured to stretch open any face mask installed thereon by providing opposing tension forces to the ear loops of the mask;
   a first set of UV lamps disposed at one or more positions on the first surface within the interior region and angled to direct illumination towards the second surface of the interior region;
   a second set of UV lamps disposed at one or more positions on the second surface within the interior region and angled to direct illumination towards the first surface of the interior region; and
   wherein each of the ear loop fastening elements comprises a pair of moveable wing elements coupled to a central hinge and configured to fold inwards towards one another in response to actuation by a user.

2. The sanitation device of claim 1, wherein one or more of the winged elements comprise a magnetized portion for coupling with one or more fixing accessories to hold items of various shapes and sizes in position within the interior region during a sanitation cycle.

3. The sanitation device of claim 1, wherein one of the first set of UV lamps, the second set of UV lamps, or both include UV LEDs.

4. The sanitation device of claim 1, wherein the interior region formed by the first and second surfaces comprises one or more reflective surfaces for reflecting UV light emissions from the UV lamps within the interior region.

5. The sanitation device of claim 1, further comprising: a controller and at least one safety sensor configured to detect a change in physical position of the hinged lid with respect to the container housing or an ambient light level above a predefined threshold indicating the hinged lid is not fully forming a closed interior region with the container housing, and
   wherein, in response to a detection form the at least one safety sensor that the hinged lid is not in a fully close position, the controller is configured to decouple the first set of UV lamps and the second set of UV lamps from a power source.

6. The sanitation device of claim 5, further comprising a user interface and display comprising buttons and lights, or a touchscreen, electrically coupled to the controller and being configured to receive one or more user inputs for initiating a sanitation cycle, the controller being configured in response to said input to power on the first set of UV lamps, the second set of UV lamps, and to start a timer and cause a time remaining until the end of the sanitation cycle to be displayed.

7. The sanitation device of claim 6, wherein the time of each sanitation cycle is stored within a memory accessible by the controller, and containing a number of predefined sanitation cycle settings and associated exposure times for different objects and sanitation intensity levels.

8. The sanitation device of claim 1, further comprising one or more magnetic elements integrated with the container housing and configured to couple with one or more fixing accessories for holding items to be sanitized in place within the interior region.

* * * * *